United States Patent [19]

Enomoto et al.

[11] Patent Number: 4,659,734

[45] Date of Patent: Apr. 21, 1987

[54] OLINECARBOXYLIC ACID DERIVATIVES

[75] Inventors: Hiroshi Enomoto, Nagaokakyo; Masahiro Kise, Nakakyo; Masakuni Ozaki, Joyo; Masahiko Kitano; Iwao Morita, both of Kyoto, all of Japan

[73] Assignee: Nippon Shinyaku Co., Ltd., Japan

[21] Appl. No.: 523,329

[22] Filed: Aug. 15, 1983

[51] Int. Cl.$^4$ .................. A61K 31/495; C07D 417/14
[52] U.S. Cl. .................................. 514/255; 514/210; 514/211; 514/212; 514/218; 514/222; 514/226; 514/231; 514/254; 540/468; 540/544; 540/546; 540/547; 540/575; 540/600; 544/54; 544/58.6; 544/58.7; 544/361; 546/62; 546/65; 546/80; 546/92
[58] Field of Search ............... 544/361, 54, 58.6, 58.7; 546/62, 65, 80, 93; 540/468, 544, 546, 547, 575, 600; 514/255, 210, 211, 212, 218, 222, 226, 231, 254

[56] References Cited

U.S. PATENT DOCUMENTS 4,426,381  1/1984  Matsumura et al. ............... 544/361
4,550,104  10/1985 Mich et al. ........................ 514/210

FOREIGN PATENT DOCUMENTS 0058392  8/1982  European Pat. Off. ............ 544/361

OTHER PUBLICATIONS

Chu, et al., "Chemical Abstracts", vol. 105(7), 1986, Col. 105:60558j.

Primary Examiner—Glennon H. Hollrah
Assistant Examiner—James H. Turnipseed
Attorney, Agent, or Firm—Jacobs & Jacobs

[57] ABSTRACT

A compound of the formula

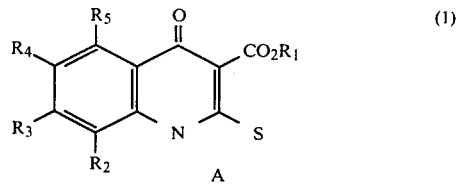

$R_1$ is hydrogen, alkali metal, alkaline earth metal, lower alkyl, pivaloyloxymethyl or phthalidyl;

$R_2$, $R_3$, $R_4$ and $R_5$ are the same or different and are hydrogen, halogen, lower alkoxy or

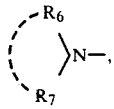

wherein $R_6$ and $R_7$ are lower alkyl or $R_6$ and $R_7$ together with the nitrogen atom to which they are attached form a five- to seven-membered unsubstituted or substituted heterocyclic ring containing said nitrogen atom as the sole hetero atom or containing nitrogen, sulfur or oxygen as additional hetereo atoms;

A is a saturated or unsaturated hydrocarbon chain of one to five carbon atoms, unsubstituted or substituted by lower alkyl; lower alkoxy; lower alkylthio; hydroxy; halogen; lower alkyl substituted by halogen, amino, loweralkoxycarbonyl, carboxy, lower-alkoxy, loweralkylthio, loweracyloxy or hydroxy; loweralkylamino; carboxy; nitro; cyano; carbonyl; imino; or by substituted or unsubstituted phenyl, phenylthio, phenylamino or phenoxy; and $R_2$ and $R_3$ or $R_3$ and $R_4$ or $R_4$ and $R_5$ together may be alkylenedioxy of 1 to 5 carbon atoms which form a ring with the carbon atoms to which they are attached; or a pharmaceutically acceptable salt thereof.

14 Claims, No Drawings

OLINECARBOXYLIC ACID DERIVATIVES

The present invention relates to novel substituted quinolinecarboxylic acid derivatives having antibacterial activity. More particularly, it relates to compounds represented by formula (I)

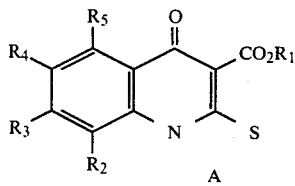

$R_1$ is hydrogen, alkali metal, alkaline earth metal, lower alkyl, pivaloyloxymethyl or phthalidyl;

$R_2$, $R_3$, $R_4$ and $R_5$ are the same or different and are hydrogen, halogen, lower alkoxy or

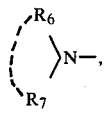

wherein $R_6$ and $R_7$ are lower alkyl or $R_6$ and $R_7$, together with the nitrogen atom to which they are attached form a five- to seven-membered heterocyclic ring containing said nitrogen atom as the sole hetero atom or containing nitrogen, sulfur or oxygen as additional hetero atoms;

A is a saturated or unsaturated hydrocarbon chain of one to five carbon atoms, unsubstituted or substituted by lower alkyl; lower alkoxy; lower alkylthio, hydroxy; halogen; lower alkyl substituted by halogen, amino, loweralkoxycarbonyl, carboxy, lower-alkoxy, loweralkylthio, loweracyloxy or by hydroxy; loweralkylamino; carboxy; nitro; cyano; carbonyl; imino; substituted or unsubstituted phenyl or phenoxy; and $R_2$ and $R_3$ or $R_3$ and $R_4$ or $R_4$ and $R_5$ together may be alkylenedioxy of 1 to 5 carbon atoms which form a ring with the carbon atoms to which they are attached; or a pharmaceutically acceptable salt thereof.

As used herein, the terms, alkyl, alkoxy and acyloxy mean alkyl, alkoxy and acyloxy of 1–10 carbon atoms. The terms "lower alkyl", "lower alkoxy" and "lower acyloxy" mean such groups of 1 to 4, preferably 1 to 3 carbon atoms. As used herein, halogen is preferably fluorine, chlorine and bromine, "alkali metal" is preferably lithium, sodium and potassium, and alkaline earth metal is calcium. Preferably, alkylenedioxy is of 1 to 3 carbon atoms, most preferably methylenedioxy. The term "alkenyl" means alkenyl of 2 to 10 carbon atoms, and the term lower alkenyl means alkenyl of 2 to 5, preferably 2 to 4 carbon atoms.

Suitable pharmaceutically acceptable salts of compound (I) are, for example, metal salts, such as the lithium, sodium, potassium or calcium salt and the like; organic base salts, such as the ethanolamine salt, diethanolamine salt and the like; inorganic acid salts, such as the hydrochloride, sulfate, phosphate and the like; and organic acid salts, such as the acetate, methanesulfonate, succinate, lactate and the like.

Nalidixic acid, piromidic acid and pipemidic acid have been widely used as synthetic antibacterial agents for the therapy of diseases infected by Gram negative bacteria. However, such agents are not satisfactory for treatment of diseases caused by Pseudomonas aeginosa or by Gram positive bacteria. Other antibacterial agents include 6-halogeno-1-substituted-7-(4-substituted piperazino)-4-oxo-1,4-dihydroquinoline-3-carboxylic acid derivatives (Japanese published applications Nos. Sho 53-65887, 53-141286, 54-66686 and 55047658) and 6-fluoro-1,8-naphthylidine derivatives (Japanese published application No. Sho 55-83785). However, among the many synthetic antibacterial agents, there is no substituted quinoline-carboxylic acid having a substituent at the 2-position.

Journal of Medicinal Chemistry, volume 20, page 791, (1977) and volume 21, page 485, (1978) and Journal of Heterocyclic Chemistry, volume 17, page 1729 (1980) disclose compounds of the above type having methyl or hydroxyl group at 2-position or the compounds in which a nitrogen atom at 1-position is bonded with the 2-position forming a ring. However, these compounds do not show marked antibacterial activity.

We have now found that the compounds (I) of the invention, which have an entirely new skeletal structure, demonstrate excellent antibacterial activity, not only against Pseudomonas aeruginosa, but also against both Gram positive and Gram negative bacteria in small doses. Compounds (I) are preferably administered to animals, including humans, orally or by injection.

Compounds (I) of the invention may be prepared by the following illustrative reaction scheme. First, an ethyl 4-oxo-1,4-dihydroquinoline-3-carboxylate derivative (VII) is prepared as follows:

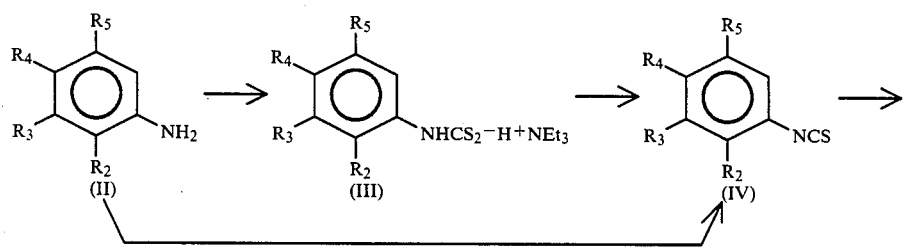

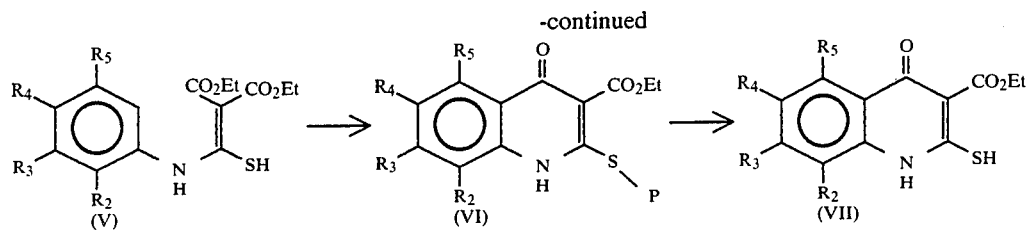

In the above formulas, $R_2$, $R_3$, $R_4$ and $R_5$ are as defined above for compound (I) and (P) is a protective group defined hereinafter. In the above reaction scheme, a substituted aniline (II), in a suitable solvent, such as benzene, or without a solvent, is reacted with carbon disulfide with cooling in the presence of a large excess of triethylamine or in the presence of amine compounds other than triethylamine and alkali metals to give the substituted phenyldithiocarbamic acid salt (III). Compound (III) is shown as having been made with an excess of triethylamine, for ease of illustration. The salt (III) is then reacted with ethyl chlorocarbonate in a solvent, such as chloroform or methylene chloride, in the presence of triethylamine or is reacted with copper sulfate, lead nitrate, iron sulfate, zinc sulfate or the like to give the substituted phenyl isothiocyanate (IV). Compound (IV) can also be manufactured directly from (II) by known methods, e.g. as disclosed in Organic Syntheses, Collective Volume I, page 447.

Reaction of the resulting compound (IV) with sodium salt of diethyl malonate provides diethyl substituted phenylaminomercaptomethylenemalonate (V). This is protected with a protective group generally used for protecting thiols (cf. The Chemistry of the Thio Group, Part Two, edited by Soul Patai, published by John Wiley and Sons, Page 669, 1974) or is protected by substituted alkyls by known methods and the resulting protected compound (not shown) is heated in a high boiling solvent, such as dichlorobenzene, tetraline, diphenyl ether, diethyleneglycol, dimethyl ether, and the like so as to effect the ring closure and thus provide compound (VI).

Suitable protective groups (P) include substituted benzyl, alkoxymethyl, 2,4-dinitrophenyl, disulfide as a dimer of (V), alkylthiomethyl, substituted carbamoyl, diphenylmethyl, triphenylmethyl, picolyl, acetamidomethyl, $\beta,\beta,\beta$-trifluoroalpha-acylaminoethyl, $\beta,\beta$-diethoxycarbonylethyl, acetyl, benzoyl, benzyloxycarbonyl, tetrahydropyranyl, benzylthiomethyl, phenylthiomethyl, isobutyloxymethyl, and the like. Using $C_1$–$C_6$ alkoxy substituted benzyl as an example, the reaction will be illustrated in more detail.

Thus, p-methoxybenzyl chloride is caused to react with (V) in the presence of an alkali, such as sodium carbonate or potassium carbonate, in a solvent such as acetonitrile, dimethyl formamide, tetrahydrofuran and the like, and the resulting product is heated in a high boiling solvent, such as diphenyl ether, so that the ring closure takes place to give the desired (VI) quantitatively.

When the resulting (VI) is treated to remove the protective group, then (VII), which is a very important intermediate compound, is obtained in high yields, For example, when the p-methoxybenzyl derivative of (VI) is used, it is treated with methanesulfonic acid, trifuloromethane sulfonic acid, trifluoroacetic acid, or a mixture thereof and anisole with cooling whereupon the protective group is removed in high yields.

As shown in the following reaction scheme, resulting (VII) may be reacted with a dihalide X-A-Y (XIII), in which Y is halogen and A is as above defined), in dimethyl formamide solvent and in the presence of potassium carbonate, to give compounds (VIII), which have a sulfur atom and the nitrogen atom of the 2-mercaptoquinoline skeleton in the same ring:

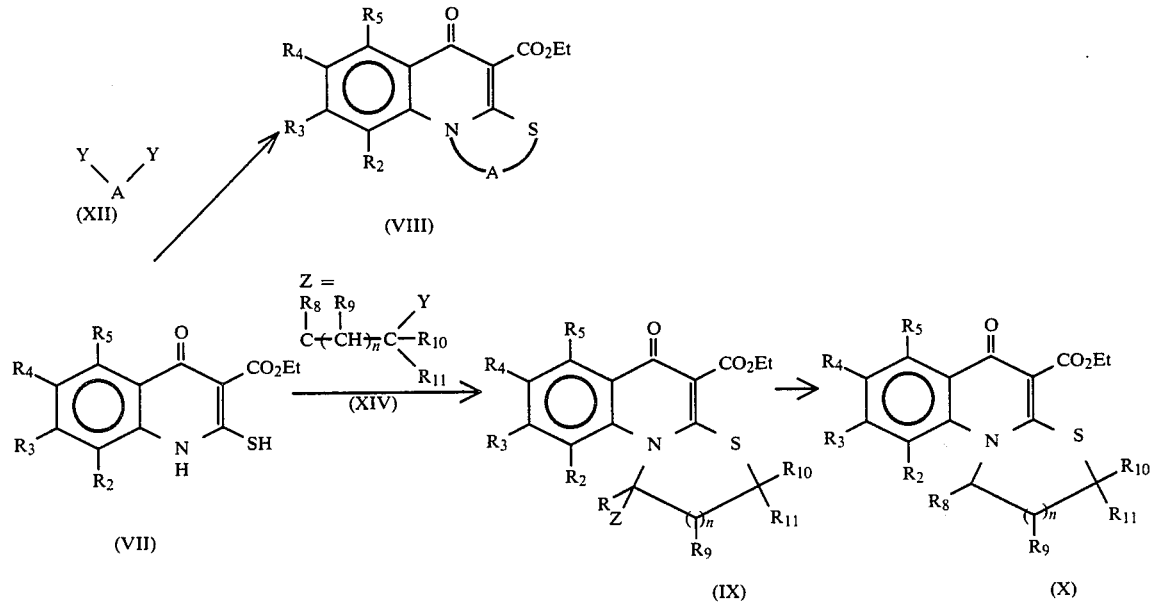

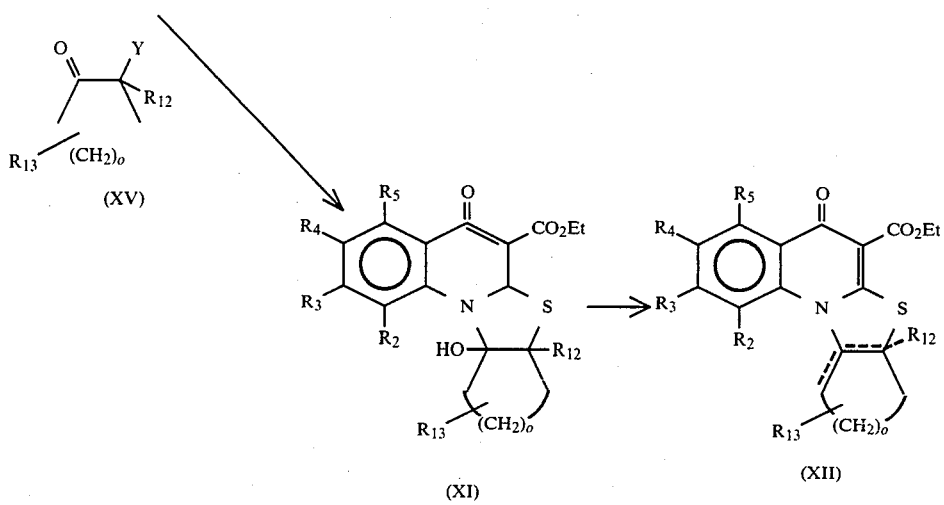

In these formulas, $R_2$, $R_3$, $R_4$, $R_5$ and A are as previously defined. $R_8$ is hydrogen, lower alkyl, halogeno-substituted alkyl, substituted phenyl, substituted benzyl, substituted alkoxy, substituted phenoxy, substituted alkylthio, substituted phenylthio, or other thio group having heterocyclic ring such as tetrazole or thiadiazole; $R_9$, $R_{10}$, $R_{11}$, $R_{12}$ and $R_{13}$ are hydrogen, lower alkyl or substituted phenyl; Z is oxygen or alkoxy; Y is halogen, and n and o are integers of 0, 1 or 2. When n is zero, there is a five-membered ring which provides a thiazoloquinoline ring and. therefore, one of $R_{10}$ and $R_{11}$ will not be present. When Z is oxygen, the Z in (IX) will become ZH by incorporating a hydrogen atom. With reference to the position of the double bond in (XII), when $R_{12}$ is H, the double bond "endo" and $R_{12}$ will not be present, and, when $R_{12}$ is other than H, the double bond is "exo", and $R_{12}$ will be present.

Compound (VII) may also be reacted with compound (XIV) or (XV) to provide compounds (IX) and (XI), respectively, which possess a hydroxyl or alkoxy group as a subtituent in the ring. Treatment of (IX) and (XI) with mineral acids, such as sulfuric acid, hydrochloric acid, nitric acid, and the like provides compounds (X) and (XII), respectively, which possess an unsaturated bond in the ring.

The resulting (VIII), (IX), (X), (XI), and (XII) may be hydrolyzed with sodium hydroxide or potassium hydroxide in an alcohol or hydrolyzed with concentrated sulfuric acid or concentrated hydrochloric acid to give the desired carboxylic acid in high yields.

When $R_3$ is halogen, compounds (VIII) to (XII) may be reacted with secondary amines of the formula

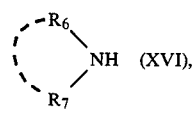

to give compounds (XVII) to (XXI) as shown below. $R_6$ and $R_7$ are the same or different and are lower alkyl or together form a heterocyclic ring of five to seven members with the nitrogen atom to which they are attached. This heterocyclic ring may also contain other heteroatoms, such as nitrogen, oxygen and sulfur, and it may be substituted or in salt form.

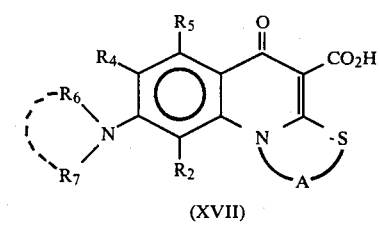

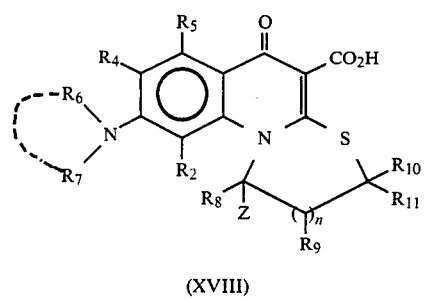

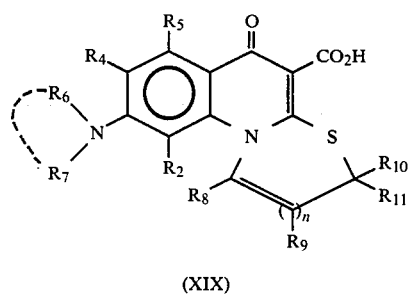

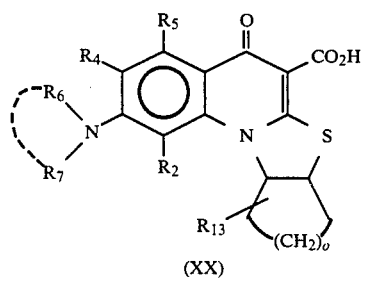

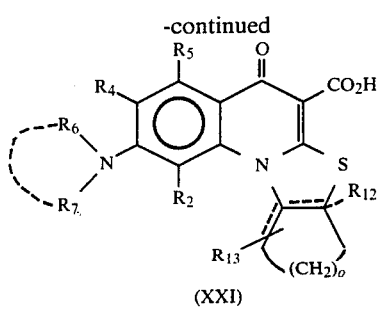

(XXI)

The carboxylic acids obtained from (IX) to (XII) may also be condensed with the secondary amine (XVI) when $R_5$ is halogen. Further, when $R_4$ is fluorine and $R_3$ is chlorine, these carboxylic acids may be reacted with compound (XVI) under controlled reaction conditions to replace the fluorine with

in which case $R_4$ in compound (I) becomes the

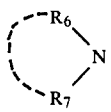

group.

The final compound (I) may be oxidized by known methods to give the corresponding sulfoxides and sulfones. Also, it can be changed to the corresponding sulfylimine, sulfoxyimine, etc. by known methods.

Compounds (VIII) and (XXIV) may be formed from compound (V) by the following reaction steps.

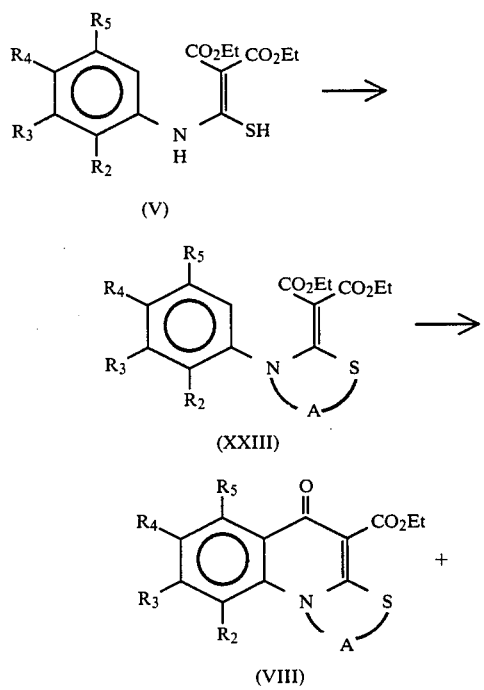

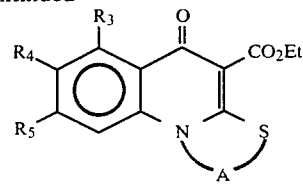

(XXIV)

Thus, instead of reacting compound (V) with the protecting group ⓟ, compound (V) is reacted with the dihalide X-A-Y (XIII) in dimethyl formamide solvent in the presence of potassium carbonate, or compound (V) is reacted with compound (XIV) or (XV) followed by a treatment with sulfuric acid or with hydrochloric acid, to provide (XXIII). Cyclization of compound (XXIII) to form (VIII) can be effected by various known cyclization reactions, such as by heating, by the use of acidic materials, such as phosphorus oxychloride, phosphorus pentachloride, phosphorous trichloride, thionyl chloride, concentrated sulfuric acid, polyphosphoric acid, polyphosphoric acid esters, and the like, etc. Cyclization by the use of acidic materials may, for example, be done by the use of equimolar to large excess amounts of the acidic material. Molar ratios of acidic material to (XXIII) may be from 10 to 20. When heating is used, such heating may be at 100° to 150° C. for 0.5 to 2 hours. When $R_2$ is hydrogen compound, (XXIV) as well as (VIII) will be formed as cyclization products. Separation of (VIII) and (XXIV) from their mixture can be effected by conventional methods, such as, for example, recrystallization or column chromatography.

When A is ethylene in compound (I), the following reaction scheme may be used:

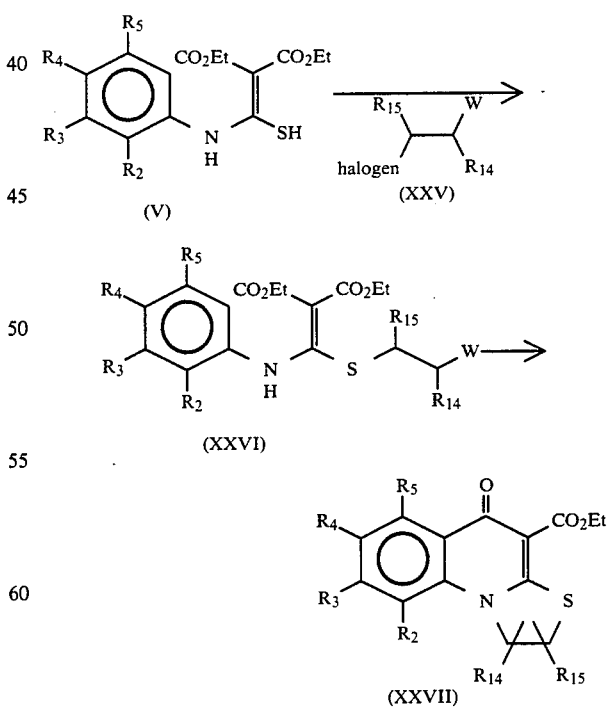

$R_2$, $R_3$, $R_4$ and $R_5$ are as already defined; $R_{14}$ and $R_{15}$ are hydrogen or lower alkyl; and W is hydroxyl, alkoxy, acetoxy, trimethylsilyloxy, alkylthio or substituted amino. In this scheme, (v) is reacted with a substituted ethylene halide (XXV) to provide compound (XXVI), which is heated in a high boiling solvent, such as dichlorobenzene, tetraline, diphenyl ether, diethyleneglycol dimethyl ether, and the like, to provide (XVII) in high yields.

Another convenient method in which no protective group for sulfur is used is as follows. Thus, compound (V) is reacted with (XIV) in the presence of potassium carbonate as an acid-removing agent in a solvent, such as dimethyl formamide or acetonitrile, to give compound (XXVIII), which is then heated in a high boiling solvent, such as dichlorobenzene, tetraline, diphenyl ether, diethylene glycol dimethyl ether, and the like, to give (XXIX) in high yields.

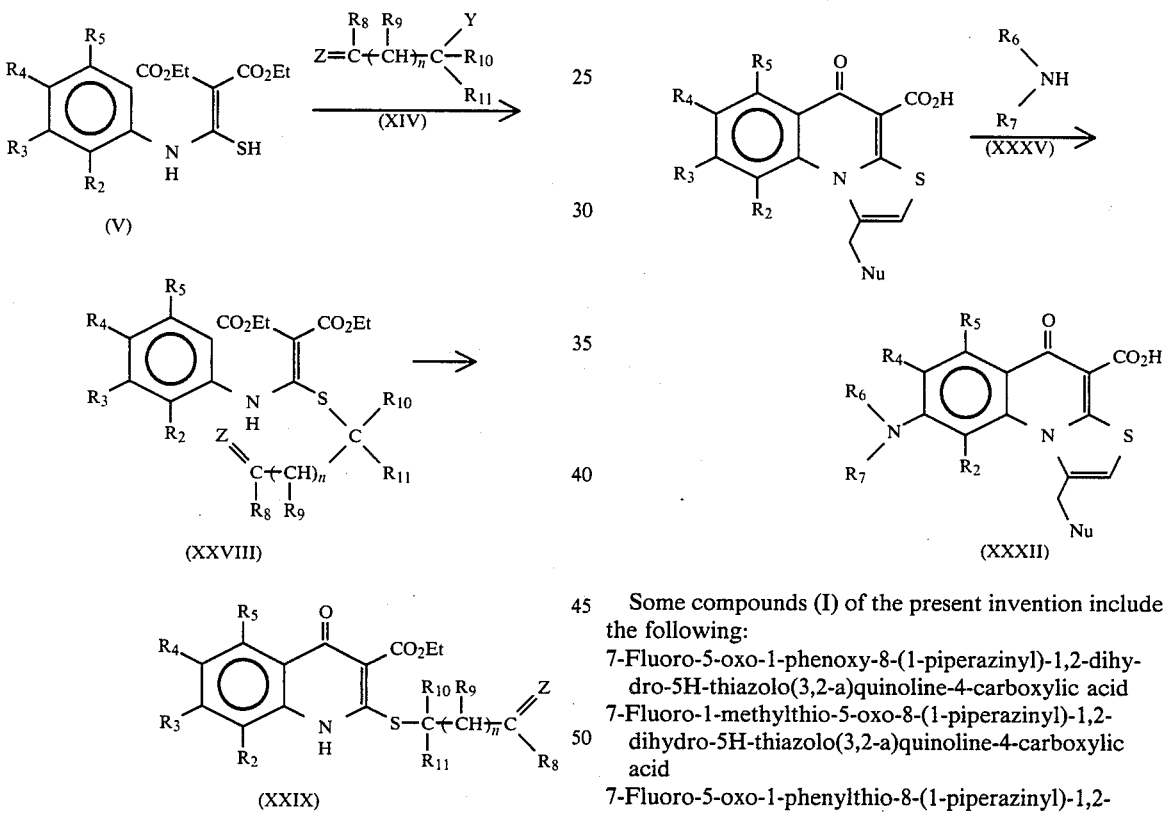

When the resulting (XXIX) is treated with an acidic material, such as concentrated hydrochloric acid or concentrated sulfuric acid, the aforementioned (IX) and (X) can be manufactured in high yields and low cost.

In the above reaction of (V) and (XIV), when (XIV) is dichloroacetone, the resulting compound (XXX), shown below, may be reacted with a reagent (Nu) such as an amine, mercaptan, alcohol and the like to produce (XXXI), which is hydrolyzed to form (XXXV), which is then reacted with (XVI) to give (XXXII) in high yields.

Some compounds (I) of the present invention include the following:
7-Fluoro-5-oxo-1-phenoxy-8-(1-piperazinyl)-1,2-dihydro-5H-thiazolo(3,2-a)quinoline-4-carboxylic acid
7-Fluoro-1-methylthio-5-oxo-8-(1-piperazinyl)-1,2-dihydro-5H-thiazolo(3,2-a)quinoline-4-carboxylic acid
7-Fluoro-5-oxo-1-phenylthio-8-(1-piperazinyl)-1,2-dihydro-5H-thiazolo(3,2-a)quinoline-4-carboxylic acid
7-Fluoro-1-methylthiomethyl-5-oxo-8-(1-piperazinyl)-1,2-dihydro-5H-thiazolo(3,2-a)quinoline-4-carboxylic acid
7-Fluoro-5-oxo-8-(1-piperazinyl)-1,2-dihydro-5H-thiazolo(3,2-a)-quinoline-2,4-dicarboxylic acid
7-Fluoro-1-hydroxy-5-oxo-8-(1-piperazinyl)-5H-thiazolo(3,2-a)-quinoline-4-carboxylic acid
7-Fluoro-1-methoxy-5-oxo-8-(1-piperazinyl)-5H-thiazoo(3,2-a)-quinoline-4-carboxylic acid
7-Fluoro-1-methylthio-5-oxo-8-(1-piperazinyl)-5H-thiazolo(3,2-a)quinoline-4-carboxylic acid.
1-Chloro-7-fluoro-5-oxo-8-(1-piperazinyl)-5H-thiazolo(3,2-a)quinoline-4-carboxylic acid.

7-Fluoro-1-methylthiomethyl-5-oxo-8-(1-piperazinyl)-5H-thiazolo-(3,2-a)quinoline-4-carboxylic acid.

1-Dimethylamino-7-fluoro-5-oxo-8-(1-piperazinyl)-5H-thiazolo(3,2-a)quinoline-4-carboxylic acid.

7-Fluoro-5-oxo-8-(1-piperazinyl)-5H-thiazolo(3,2-a)quinoline-1,4-dicarboxylic acid.

7-Fluoro-1-nitro-5-oxo-8-(1-piperazinyl)-5H-thiazolo(3,2-a)quinoline-4-carboxylic acid.

1-Cyano-7-fluoro-5-oxo-8-(1-piperazinyl)-5H-thiazolo(3,2-a)quinoline-4-carboxylic acid.

7-Fluoro-2-hydroxy-5-oxo-8-(1-piperazinyl)-5H-thiazolo(3,2-a)quinoline-4-carboxylic acid.

7-Fluoro-2-methoxy-5-oxo-8-(1-piperazinyl)-5H-thiazolo(3,2-a)quinoline-4-carboxylic acid.

7-Fluoro-5-oxo-8-(1-piperazinyl)-5H-thiazolo(3,2-a)quinoline-2,4-dicarboxylic acid.

The biological properties of the compounds of the present invention are as follows.

(1) Antibacterial spectra of the compounds of the present invention.

The Antibacterial activity of the compounds of Examples 14, 13, 22b, 21 and 15 was determined in accordance with the method of Japan Chemotherapeutic Society (cf. Nippon Kagaku Ryoho Gakkai Shi, volume 29, number 1, pages 76 to 79, 1981) and the results are reported in Table 1, which follows.

As is apparent from Table 1, compounds (I) had strong activity against both Gram positive and Gram negative bacteria including Pseudomonas aeruginosa and showed stronger antibacterial activity than 1-ethyl-6-fluoro-7-(1-piperazinyl)-4-oxo-1,4-dihydroquinoline-3-carboxylic acid, which was used as a comparison.

TABLE I

| Names of Microorganisms Tested | Gram | Compounds Tested (indicated by example numbers) Minimum Growth Inhibiting Concn ($\mu$g/ml) | | | | |
|---|---|---|---|---|---|---|
| | | 14 | 13 | 22b | 21 | 15 |
| Staphylococcus aureus 209-PJC | + | 0.1 | 0.025 | 0.013 | 0.025 | 0.025 |
| Staphylococcus aureus Smith | + | 0.05 | 0.05 | 0.053 | 0.013 | 0.013 |
| Micrococcus luteus ATCC 9341 | + | 0.78 | 0.78 | 0.78 | 0.39 | 1.56 |
| Streptococcus pyogenes S-23* | + | 0.2 | 0.1 | 0.2 | 0.1 | 0.1 |
| Streptococcus pneumoniae Type I* | + | 0.2 | 0.1 | 0.39 | 0.2 | 0.39 |
| Bacillus subtilis ATCC 6633* | + | 0.0063 | 0.0063 | 0.0008 | 0.0063 | 0.0063 |
| Listeria monocytogenes RIMD 1205020 | + | 1.56 | 0.2 | 0.2 | 0.2 | 0.39 |
| Escherichia coli NIHJ JC-2 | − | 0.1 | 0.05 | 0.025 | 0.025 | 0.2 |
| Escherichia coli KC-14 | − | 0.013 | 0.0063 | 0.013 | 0.0063 | 0.05 |
| Klebsiella pneumoniae K-1966 | − | 0.1 | 0.025 | 0.05 | 0.013 | 0.05 |
| Serracia marcescens IFO 3736 | − | 0.39 | 0.2 | 0.39 | 0.2 | 0.39 |
| Proteus mirabilis 181 | − | 0.013 | 0.0063 | 0.2 | 0.05 | 0.2 |
| Proteus vulgaris DX-19 | − | 0.0063 | 0.013 | 0.1 | 0.0016 | 0.05 |
| Pseudomonas aeruginosa No. 12 | − | 0.39 | 0.2 | 0.78 | 0.39 | 0.78 |
| Pseudomonas aeruginosa E-2 | − | 0.39 | 0.2 | 0.39 | 0.39 | 1.56 |
| Pseudomonas cepacia ATCC 25416 | − | 0.78 | 0.78 | 0.2 | 0.2 | 1.56 |
| Pseudomonas maltophilia ATCC 13637 | − | 0.025 | 0.5 | 0.025 | 0.013 | 0.0063 |
| Alcaligenes faecalis ATCC 8750 | − | 0.78 | 0.78 | 0.78 | 0.78 | 0.78 |
| Acinetobacter calcoacelicus 54 | − | 0.39 | 0.78 | 0.2 | 0.2 | 0.39 |

*5% Horse blood added agar medium for sensitivity measurement being used.

(2) Anti-Bacterial Activity ddY—Strain mice (male; body weight 20±1 grams) of SPF were innoculated with the bacteria set forth in Table 2 by administration of a supension of the bacterial in 4% mucin solution into the abdominal cavity. A compound of the invention was given one time per os two hours after the infection, and, from the survival rate after one week. 50% effective doses (ED$_{50}$) were calculated by the Behrens-Karber method. The test results are given in Table 2. It has thereby been found that the compound of the present invention showed stronger preventive effect as compared with 1-ethyl-6-fluoro-7-(1-piperazinyl)-4-oxo-1,4-dihydroquinoline-3-carboxylic acid, which was used as a comparison compound. Also, it has been found that the present invention compounds exhibit marked therapeutic effect against infections caused by Gram positive bacteria.

TABLE 2

| BACTERIA | Amount of Bacteria Infected (per mouse) | Names of Compounds Tested (indicated by example numbers) ED$_{50}$ in mg/kg | | | |
|---|---|---|---|---|---|
| | | 14 | 22b | 15 | Comparison Compd. |
| Pseudomonas aeruginosa E-2 | 2 × 10$^5$ | 16.0 | 13.1 | 10.7 | 260 |
| Escherichia coli KC-14 | 5 × 10$^4$ | 1.5 | 1.1 | 2.0 | 3.3 |
| Klebsiella pneumoniae K-1966 | 3 × 10$^3$ | — | 2.7 | 3.3 | >13.0 |

TABLE 2-continued

| BACTERIA | Amount of Bacteria Infected (per mouse) | Names of Compounds Tested (indicated by example numbers) $ED_{50}$ in mg/kg | | | Comparison Compd. |
|---|---|---|---|---|---|
| | | 14 | 22b | 15 | |
| *Serracia marcescens* T-55 | $5 \times 10^6$ | — | 5.4 | — | 6.0 |
| *Proteus mirabilis* 181 | $2 \times 10^7$ | — | 13.0 | — | 29.0 |
| *Acimetobacter calcoaceticus* | $1 \times 10^7$ | — | 17.5 | >35.0 | >35.0 |
| *Staphylococcus aureus* Smith | $3 \times 10^6$ | — | 2.4 | — | >25.0 |

(3) Effect of the compounds of the present invention against ascending urinary tract infection.

ICR Female mice (body weight 20±1 grams) of SPE strain were used in the experiments. The mice were not given any water for seventeen hours, then compulsorily urinated, anesthesized by the administration of 60 mg/kg of pentobarbital into the abdominal cavity, then $1.5 \times 10^5$ of Pseudomonas aeruginosa E-2 strain were impregnated into the bladder via the urinary tract, and the external urinary meatus was stopped for four hours by a pin clip, whereupon the mice were infected in the ascending urinary tract.

The compound of Example 22b was given once orally, 4 hours after infection, then twice a day, and the administration was continued for three days. On the fourth day, the kidney was isolated, homogenized in a physiological saline solution, and the number of bacteria was calculated on suitable medium such as, for example, Drigalski medium. If the number of bacteria per one gram of kidney was less than 104, then the compound was judged as "effective". The results are given in Table 3.

The compound of the present invention exhibited marked therapeutic effect in lower doses as compared with 1-ethyl-6-fluoro-7-(1-piperazinyl)-4-oxo-1,4-dihydroquinoline-3-carboxylic acid which was used as a comparison compound.

TABLE 3

| Doses Administered (mg/kg) | Number Of Mice Where Compound Was Effective/Total Mice Tested | |
|---|---|---|
| | Compound of Ex. 22b | Comparison Compound |
| 100 | 7/7 | 6/7 |
| 50 | 7/7 | 4/7 |
| 25 | 6/7 | 1/7 |
| 12.5 | 4/7 | 0/7 |
| 6.25 | 4/7 | 0/7 |
| 3.13 | 1/7 | 0/7 |
| 50% Effective Dose: | 8 mg/kg | 58 mg/kg |

(4) Blood serum concentration of the compound of Example 22b.

In this experiment, ddY strain mice (male; body weight 30±2 grams) were used. Sixty mg/kg of the compound of Example 22b were given per os. The blood concentration was calculated from calibration curves obtained by the disc method using Escherichia coli NIHJ strain as tested bacteria and diluting the test compound of mice serum. Table 4 reports the concentration of the test compound in blood serum with respect to time. It is apparent that the compound of the present invention promptly gave high and sustained blood concentrations when administered orally.

TABLE 4

| Time Elapsed (hours) | Concentration in Blood Serum ($\mu$g/ml) Average ± Standard Error | |
|---|---|---|
| | Compd of Ex 22b | Comparison Compd* |
| 0.25 | 3.4 ± 0.82 | 0.64 ± 0.09 |
| 0.5 | 5.4 ± 0.32 | 0.90 ± 0.29 |
| 1 | 4.2 ± 0.70 | 0.58 ± 0.10 |
| 2 | 3.3 ± 0.37 | 0.33 ± 0.15 |
| 4 | 2.5 ± 0.23 | 0.09 ± 0.01 |

*1-Ethyl-6-fluoro-7-(1-piperazinyl)-4-oxo-1,4-dihydroquinoline-3-carboxylic acid (5) Excretion into urine and recovery.

In the measurement of excretion into urine, ddY strain mice (male; body weights 30±2 grams) were used. Sixty mg/kg of the compound of Example 22b was administered per os and the mice were fed in metabolic cages and their urine was collected.

It was thereby found that the compound of Example 22b was metabolized to the compound of Example 21, and was excreted into urine almost completely. Therefore, in the quantitative determination, the calibration curve of the compound of Example 21, calculated by the disc method using Escherichia coli NIHJ strain and using the compound dissolved in phosphoric acid buffer (pH 8.0; 1/15M) was used. Table 5 reports the excretion into urine with respect to time, total recovery amount and recovery rate of the compound of Example 22b. It is apparent that the present invention compound is excreted into urine promptly and in high concentration which is continued and exhibits high recovery rate.

TABLE 5

| | Amount excreted into Urine ($\mu$g) Average ± Standard Error | |
|---|---|---|
| | Compd of Ex 22b | Comparison Compd* |
| 0-3 hrs | 268.1 ± 84.4 | 60.25 ± 17.9 |
| 3-6 | 108.3 ± 33.1 | 29.25 ± 9.0 |
| 6-24 | 437.5 ± 21.8 | 19.78 ± 6.6 |
| Total Recovery | 813.9 $\mu$g | 109.3 $\mu$g |
| Recovery Rate | 40.7% | 5.46% |

*1-Ethyl-6-fluoro-7-(1-piperazinyl)-4-oxo-1,4-dihydroquinoline-3-carboxylic acid (6) Acute Toxicity.

Groups of ten ddY strain male mice (body weights: 20±1 grams) of the test compound were orally administered to determine the LD50. The results are reported in Table 6. There was case X in which many mice died when the dose was 2000 mg/kg or less.

TABLE 6

| Compounds Tested | 50% Lethal Doses ($LD_{50}$) in mg/kg |
|---|---|
| Compd of Ex 14 | more than 2000 |
| Compd of Ex 13 | more than 2000 |
| Compd of Ex 22b | more than 2000 |
| Compd of Ex 21 | more than 2000 |
| Compd of Ex 15 | more than 2000 |

EXAMPLE 1

Ethyl 8-chloro-7-fluoro-1-(2-tetrahydropyranyloxymethyl)-5-oxo-1,2-dihydro-5H-thiazolo(3,2-a)quinoline-4-carboxylate A mixture of 6.02 grams (20 mmol) of ethyl 7-chloro-6-fluoro-4-hydroxy-2-mercaptoquinoline-3-carboxylate and 6.64 grams (22 mmol) of 1,2-dibromo-3-(2-tetrahydropyranyloxy)-propane in 50 ml of dimethylformamide was heated at 80° C. for three hours with stirring in the presence of 6.08 grams (44 mmol) of potassium carbonate (anhydrous). Dimethyl formamide was evaporated therefrom in vacuo and water was added to the residue followed by extracting with chloroform. The chloroform solution was washed with water, dried, concentrated, and purified by silica gel chromatography to give 6.53 grams of ethyl 8-chloro-7-fluoro-1-(2-tetrahydropyranyloxymethyl)-5-oxo-1,2-dihydro-5H-thiazolo(3,2-a)-quinoline-4-carboxylate. The yield was 73.9 percent. Melting point was 183° to 186° C. Elementary analysis calculated as $C_{20}H_{21}ClFNO_5S$: C 54.36, H 4.79, N 3.17; Found: C 54.18, H 4.83, N 3.34.

Infrared absorption spectra (KBr, cm$^{-1}$): 1700, 1600, 1335, 1125.

Nuclear magnetic resonance spectra δ(CDCl$_3$): 1.2–1.8 (9H, multiplet, —OCH$_2$CH$_3$, CCH$_2$CH$_2$CH$_2$C), 3.2–4.0 (6H, multiplet, SCH$_2$—, OCH$_2$×2), 4.1–4.7

(3H, multiplet, OCH$_2$CH$_3$, 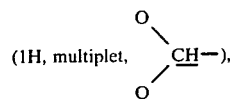

5.1–5.6 (

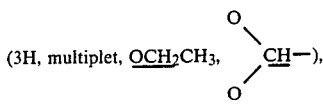

7.55 (1H, doublet, C$_9$—H), 7.98 (1H, doublet, C$_6$—H).

EXAMPLE 2

8-Chloro-7-fluoro-1-hydroxymethyl-5-oxo-1,2-dihydro-5H-thiazolo(3,2-a)quinoline-4-carboxylic acid (a) In 10 ml of ethanol was dissolved 2.20 grams (4.98)mmol) of ethyl 8-chloro-7-fluoro-1-(2-tetrahydropyranyloxymethyl)-5-oxo-1,2,-dihydro-5H-thiazolo(3,2-a)quinoline-4-carboxylate, then 252 mg (6.3 mmol) of sodium hydroxide and 20 ml of water were added thereto, and the mixture was heated to reflux for one hour and a half. This was then allowed to cool to room temperature, neutralized with acetic acid, crystals separated out therefrom were collected by filtration, and dried to give 2.00 grams of 8-chloro-7-fluoro-1-(tetrahydropyranyloxymethyl)-5-oxo-1,2-dihydro-5H-thiazole(3,2-a)quinoline-4-carboxylic acid. Yield was 97.1 percent. Melting point was 241° to 246° C. Elementary analysis calculated as $C_{18}H_{17}ClFNO_5S$: C 52.24, H 4.14, N 3.38; Found: C 53.02, H 4.49, N 3.14.

Infrared absorption spectra (KBr, cm$^{-1}$): 1700, 1595, 1125.

Nuclear magnetic resonance spectra δ(CDCl$_3$): 1.2–1.8 (6H, multiplet, C—CH$_2$CH$_2$CH$_2$—C), 3.2–4.1 (6H, multiplet, S—CH$_2$, O—CH$_2$×2), 4.35–4.6

5.2–5.7

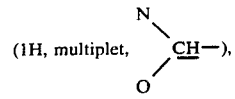

7.6–8.1 (2H, multiplet, C$_6$—H, C$_9$—H), 15.05 (1H, singlet, COOH).

(b) Ten ml of trifluoroacetic acid was cooled with ice, stirred, then 1.47 grams (3.55 mmol) of 8-chloro-7-fluoro-1-(2-tetrahydropyranyloxymethyl)-5-oxo-1,2-dihydro-5H-thiazolo(3,2-a)quinoline-4-carboxylic acid was gradually added thereto, and stirred with stirring and ice cooling for thirty minutes. Then trifluoroacetic acid was removed therefrom under reduced pressure in an ice water bath, 30 ml of water was added thereto, and crystals separated therefrom were collected by filtration and dried to give 1.16 grams of 8-chloro-7-fluoro-1-hydroxymethyl-5-oxo-1,2-dihydro-5H-thiazolo(3,2-a)quinoline-4-carboxylic acid. The yield was 99.1 percent and melting point was 314° to 316° C. (with decomposition). Elementary analysis calculated as $C_{13}H_9ClFCO_4S$: C 47.35; H 2.75, N 4.25; Found: C 47.58, H 2.83, N 4.31.

Infrared absorption spectra (KBr, cm$^{-1}$): 3600 to 3200, 1700, 1595.

Nuclear magnetic resonance δ(CF$_2$CO$_2$D): 3.1–3.7 (4H, multiplet, S—CH$_2$—, O—CH$_2$—), 5.8–6.3

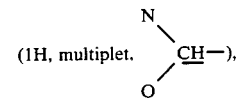

7.8–8.4 (2H, multiplet, C$_6$—H, C$_9$—H).

EXAMPLE 3

7-Fluoro-1-hydroxymethyl-8-(4-methyl-1-piperazinyl)-5oxo-1,2-dihydro-5H-thiazolo(3,2-a)quinoline-4-carboxylic acid A mixture of 0.98 gram (2.97 mmol) of 8-chloro-7-fluoro-1-hydroxymethyl-5-oxo-1,2-dihydro-5H-thiazolo-(3,2-a)lquinoline-4-carboxylic acid and 1.50 grams (14.97 mmol) of N-methylpiperazine was heated to reflux in 20 ml of pyridine for eighteen hours. Pyridine was removed therefrom under reduced pressure, then 5 ml of dimethyl formamide was added thereto, the mixture was heated so that the content was dissolved, then allowed to stand at room temperature, crystals separated therefrom were collected by filtration and were recrystallized from a mixture of trifluoroacetic acid and water to give 264 ml of the title compound. The yield was 22.6 percent and melting point was 264° to 266° C. (with decomposition). Elementary analysis calculated as $C_{18}H_{20}FN_3O_4S$: C 54.95, H 5.12, N 10.68; Found: C 55.02; H 5.31, N 10.84.

Infrared absorption spectra (KBr, cm$^{-1}$): 3310, 1700, 1630, 805.

Nuclear magnetic resonance spectra δ (CF$_3$CO$_2$D): 3.15 (3H, singlet, N—CH$_3$), 3.3–4.5

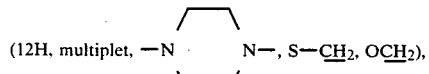
(12H, multiplet, —N⌒N—, S—C$\underline{H}_2$, OC$\underline{H}_2$), 5.9–6.3

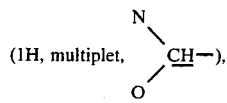
(1H, multiplet, \N-CH— / O), 7.42 (1H, doublet, C$_9$—H), 7.12 (1H, doublet, C$_6$—H).

EXAMPLE 4

Ethyl 8-chloro-1-(N,N-dimethylaminomethyl)-7-fluoro-5-oxo-1,2-dihydro-5H-thiazolo(3,2-a)quinoline-4-carboxylate A mixture of 6.02 grams (20 mmol) of ethyl 7-chloro-6-fluoro-4-hydroxy-2-mercaptoquinoline-3-carboxylate and 7.20 gram (29.4 mmol) of 1,2-dibromo-3-dimethylaminopropane was stirred in 100 ml of dimethyl formamide for fifteen hours in the presence of 9.30 grams (67.3 mmol) of potassium carbonate. Dimethyl formamide was then evaporated therefrom under reduced pressure, water was added to the residue, and extracted with chloroform. The resulting chloroform solution was washed with water, dried, concentrated, and ether was added thereto. Insoluble crystals obtained thereby were collected by filtration to give 6.84 grams of ethyl 8-chloro-1-dimethylaminomethyl-7-fluoro-5-oxo-1,2-dihydro-5H-thiazolo(3,2-a)quinoline-4-carboxylate. The yield was 89.1 percent and the melting point was 165° to 168° C. Elementary analysis calculated as C$_{17}$H$_{18}$ClFN$_2$O$_3$S: C 53.05 H 4.71, N 7.28; Found: C 53.31, H 4.50, N 7.62.

Infrared absorption spectra (Kr, cm$^{-1}$); 1705, 1595, 805.

Nuclear magnetic resonance spectra δ (CDCl$_3$): 1.41 (3H, triplet, OCH$_2$C$\underline{H}_3$), 2.36

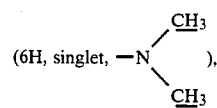
(6H, singlet, —N(CH$_3$)(CH$_3$)), 3.45–3.65 (2H, multiplet, SC$\underline{H}_2$), 4.35 (2H, quartet, OC$\underline{H}_2$CH$_3$), 4.9–5.3

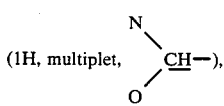
(1H, multiplet, \N-CH— / O), 7.29 (1H, doublet, C$_9$—H), 7.95 (1H, doublet, C$_6$—H).

EXAMPLE 5

8-Chloro-1-(N,N-dimethylaminomethyl)-7-fluoro-5-oxo-1,2-dihydro-5H-thiazolo(3,2-a)-quinoline-4-carboxylic acid Ethyl 8-chloro-1-dimethylaminomethyl-7-fluoro-5-oxo-1,2-dihydro-5H-thiazolo(3,2-a)quinoline-4-carboxylate (3.35 grams, 8.7 mmol) was dissolved in 40 ml of ethanol, 965 mg (24.1 mmol) of sodium hydroxide and 6 ml of water were added thereto, and the mixture was heated to reflux for forty minutes. Ethanol was removed therefrom under reduced pressure, the residue was neutralized with acetic acid, crystals separated therefrom were collected by filtration, dried, and recrystallized from dimethyl formamide to give 1.81 grams of the title product. The yield was 58.3 percent and the melting point was 214° to 216° C. Elementary analysis calculated as C$_{15}$H$_{14}$ClFN$_2$O$_3$S: C, 50.49, H 3.95, N 7.85; Found: C 50.63, H 3.78, N 7.61.

Infrared absorption spectra (KBr, cm$^{-1}$): 1705, 1959, 1045, 810.

Nuclear magnetic resonance spectra δ (CF$_3$CO$_2$D: 3.29 (3H, singlet, =N—C$\underline{H}_3$), 3.40 (3H, singlet, =N—C$\underline{H}_3$), 3.3–4.6 (4H, multiplet, S—C$\underline{H}_2$, N—C$\underline{H}_2$), 6.1–6.7

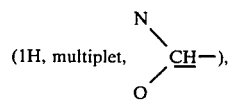
(1H, multiplet, \N-CH— / O), 8.07 (1H, doublet, C$_9$—H), 8.26 (1H, doublet, C$_6$—H).

EXAMPLE 6

1-(N,N-Dimethylaminoethyl)-7-fluoro-8-(4-methyl-1-piperazinyl)-5-oxo-1,2-dihydro-5H-thiazolo(3,2-a)-quinoline-4-carboxylic acid A mixture of 1.0 gram (2.8 mmol) of 8-chloro-1-(N,N-dimethylaminomethyl)-7-fluoro-5-oxo, 1,2-dihydro-5-H-thiazolo(3,2-a)-quinoline-4-carboxylic acid and 3.20 grams (31.9 mmol) of N-methylpiperazine was heated to reflux in 15ml of pyridine for fifteen hours. Pyridine was removed therefrom under reduced pressure, then 5 ml of dimethyl formamide was added thereto, the content was dissolved by heating, allowed to cool to room temperature, and crystals separated therefrom were collected by filtration and recrystallized from dimethyl formamide to give 384 mg of the title compound in 32.6 percent yield. Melting point was 221° to 223° C. Elementary analysis calculated as C$_{20}$H$_{25}$FN$_4$O$_3$S: C 57.13, H 5.99, N 13.32; Found: C 57.02, H 6.13, N 13.63.

Infrared absorption spectra (KBr, cm$^{-1}$): 1700, 1625, 1580, 805.

Nuclear magnetic resonance spectra δ (CF$_3$CO$_2$D): 3.18 (3H, singlet, =N—C$\underline{H}_3$), 3.25 (3H, singlet, —NC$\underline{H}_3$), 3.36

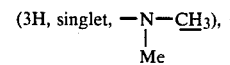
(3H, singlet, —N(Me)—C$\underline{H}_3$), 3.2–4.5

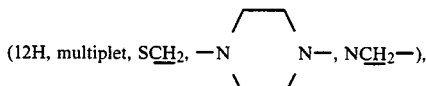
(12H, multiplet, SC$\underline{H}_2$, —N⌒N—, NC$\underline{H}_2$—), 6.3–6.7

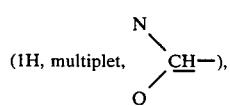
(1H, multiplet, \N-CH— / O), 7.20 (1H, doublet, C$_9$—H), 8.13 (1H, doublet, C$_6$—H).

EXAMPLE 7

Ethyl 8-chloro-7-fluoro-5-oxo-1-phenyl-1,2-dihydro-5H-thiazolo(3,2-a)quinoline-4-carboxylate In dimethyl formamide was dissolved 2.0 grams (6.6 mmol) of ethyl 7-chloro-6-fluoro-4-hydroxy-2-mercaptoquinoline-3-carboxylate and the mixture was heated at 40° C. for four hours with stirring after addition of 1.8 grams (13.2 mmol) of potassium carbonate and 2.1 grams (8.0 mmol) of (1,2-dibromoethyl)benzene. The content was concentrated under reduced pressure, water was added to the residue, extracted with chloroform, the chloroform extract was washed with water, dried, concentrated, and the resulting crystals were recrystallized from a mixture of chloroform and ether to give the title compound. The yield was 2.17 grams (81.3 percent) and the melting point was 172° C. Elementary analysis calculated as $C_{20}H_{15}ClFNO_3S$: C 59.48, H 3.84, N 3.47; Found: C 59.54, H 3.53, N 3.27.

Infrared adsorption spectra (KBr, $cm^{-1}$): 1715, 1675, 1636, 1608, 1480, 1180.

Nuclear magnetic resonance spectra $\delta$ ($CF_3CO_2D$): 1.38 (3H, triplet, $-OCH_2\underline{CH_3}$), 4.30 (2H, quartet, $-O\underline{CH_2}CH_3$), 4.40–5.30 (3H, multiplet, $C_1$—H, $C_2$—H), 7.20 (1H, doublet, $C_9$—H), 7.32 (5H, singlet, phenyl group-H), 7.90 (1H, doublet, $C_6$—H).

EXAMPLE 8

8-Chloro-7-fluoro-5-oxo-1-phenyl-1,2-dihydro-5H-thiazolo(3,2-a)-quinoline-4-carboxylic acid 8-chloro-7-fluoro-5-oxo-1-phenyl-1,2-dihydro-5H-thiazolo(3,2-a)quinoline-4-carboxylic acid ethyl ester (2.17 grams, 5.4 mmol) was suspended in a mixture of 0.43 gram (10.7 mmol) of sodium hydroxide, 30 ml of ethanol and 60 ml of water and the whole was heated to reflux for twelve hours. After cooled, the mixture was acidified with acetic acid, crystals separated out therefrom were collected by filtration, washed with water, dried with air, and recrystallized from Methyl Cellosolve to give the title compound in 1.18 grams yield (58.1 percent). Melting point was 237° to 40° C. (with decomposition). Elementary analysis calculated as $C_{18}H_{11}ClFNO_3S$: C 57.53, H 2.95, N 3.72; Found: C 57.72, H 2.64, N 3.56.

Infrared adsorption spectra (KBr, $cm^{-1}$), 1700, 1592, 1470.

Nuclear magnetic resonance spectra $\delta(CF_3CO_2D)$: 5.00–5.70 (3H, multiplet, $C_1$—H, $C_2$—H), 7.37 (5H, singlet, phenyl group-H), 7.95 (1H, doublet, $C_9$—H), 8.20 (1H, doublet, $C_6$—H).

EXAMPLE 9

8-Chloro-1-ethoxy-7-fluoro-5-oxo-1,2-dihydro-5H-thiazolo(3,2-a)-quinoline-4-carboxylic acid Ethyl 7-chloro-6-fluoro-4-hydroxy-2-mercaptoquinoline-3-carboxylate (4.0 grams, 13.3 mmol) was dissolved in 30 ml of dimethyl formamide, the mixture was stirred for awhile after addition of 3.66 grams (27 mmol) of potassium carbonate), and heated at 80° C. with stirring for eighteen hours with 3.94 grams (20 mmol) of 2-bromo-1,1-diethoxyethane. When the reaction was completed, the solvent was removed therefrom under reduced pressure, water was added to the residue, and crystals separated therefrom were extracted with ethyl acetate. The extract was washed with water, dried with magnesium sulfate, and the solvent was removed therefrom under reduced pressure to give 3.2 grams (57.5 percent) of ethyl 7-chloro-2-(2,2,-diethoxyethylthio)-6-fluoro-4-hydroxyquinoline-3-carboxylate.

Ethyl 7-chloro-2-(2,2-diethoxyethylthio)-6-fluoro-4-hydroxyquinoline-3-carboxylate (3.2 grams, 7.6 mmol) was added to 15 ml of concentrated hydrochloric acid and the mixture was stirred with heating at 90° C. When the ester was completely dissolved therein, ice water was poured thereinto, and crystals separated out therefrom, were collected by filtration whereupon 2.68 grams (94.3 percent) of ethyl 8-chloro-1-ethoxy-7-fluoro-5-oxo-1,2-dihydro-5H-thiazolo(3,2-a)-quinoline-4-carboxylate was obtained.

Ethyl 8-chloro-1-ethoxy-7-fluoro-5-oxo-1, 2-dihydro-5H-thiazolo(3,2-a)-quinoline-4-carboxylate (2.68 grams, 7.2 mmol) was dissolved in 80 ml of hot ethanol and 30 ml of 2N sodium hydroxide solution was added thereto. The mixture was heated to reflux for ten minutes, then cooled to room temperature, and insoluble matters were filtered off. The mother liquor was adjusted to pH 7.0 to 6.5 and separated crystals therefrom were collected by filtration. The crystals were then washed with water, ethanol and ether, air-dried, and the resulting crude crystals were recrystallized from dimethyl formamide to give 1.56 grams (62.4 percent) of the title compound. Melting point was 308.5° C. (with decomposition). Elementary analysis calculated as $V_{14}H_{11}ClFNO_4S$: C 48.92, H 3.23, N-4.05; Found: C 48.89, H 3.20, N 4.00.

Infrared absorption spectra (KBr, $cm^{-1}$): 1695, 1590, 1470, 810.

Nuclear magnetic resonance spectra $\delta$ ($CF_3CO_2D$): 1.31 (3H, multiplet, $-OCH_2\underline{CH_3}$), 3.50–4.30 (4H, multiplet, $-O-\underline{CH_2}CH_3$, $C_2$—H), 6.98 (1H, double doublet, $C_1$—H), 8.00–8.30 (2H, multiplet, phenyl group-H).

EXAMPLE 10

1-Ethoxy-7-fluoro-8-(4-methyl-1-piperazinyl)-5-oxo-1,2-dihydro-5H-thiazolo(3,2-a)-quinoline-4-carboxylic acid 8-chloro-1-ethoxy-7-fluoro-5-oxo-1,2-dihydro-5H-thiazolo(3,2-a)quinoline-4-carboxylic acid (800 mg, 2.32 mmol) was suspended in 20 ml of pyridine and the mixture was heated to reflux after addition of N-methylpiperazine. After thirteen hours, 4 ml more of N-methylpiperazine was added thereto, and the mixture was heated to reflux for four hours more. When the reaction was completed, pyridine was removed therefrom under reduced pressure, water was added to the residue, and crystalline substance was collected by filtration. This was recrystallized from acetonitrile to give 340 mg of the title product. Yield was 36 percent. Melting point was 266.5° C. (with decomposition). Elementary analysis calculated as $C_{19}H_{22}FN_3O_4S$: C 56.00, H 5.44, N 10.31; Found: C 56.13, H 5.58, N 10.40.

Infrared absorption spectra (KBr, $cm^{-1}$): 1700, 1630, 1490.

Nuclear magentic resonance spectra $\delta$ ($CF_3CO_2D$): 1.29 (3H, triplet, $-OCH_2\underline{CH_3}$), 3.11 (3H, singlet, $NCH_3$), 3.35–4.50

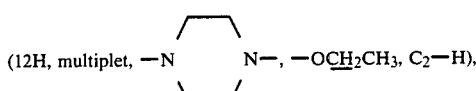

(12H, multiplet, $-N\underset{\underline{\phantom{xx}}}{\overset{\frown}{\phantom{xx}}}N-$, $-O\underline{CH_2}CH_3$, $C_2$—H), 6.90–7.25 (1H, multiplet, $C_1$—H), 7.38 (1H, wide doublet, $C_9$—H), 8.14 (1H, doublet, $C_6$—H).

EXAMPLE 11

Ethyl 8-chloro-7-fluoro-5-oxo-5H-thiazolo(3,2-a)quinoline-4-carboxylate

Ethyl 7-chloro-6-fluoro-4-hydroxy-2-mercaptoquinoline-carboxylate (3.0 grams, 10 mmol) was dissolved in 20 ml of dimethyl formamide and the solution was heated to reflux at 80° C. for twelve hours after addition of 2.7 grams of potassium carbonate and 2.9 grams (15 mmol) of bromoacetaldehyde diethyl acetal. The content was concentrated under reduced pressure, water was added to the residue, then extracted with ethyl acetate, and the extract was washed with water and concentrated to give 4.3 grams of crystalline residue. To this was added 22.0 grams of concentrated sulfuric acid, the mixture was heated with stirring at 90° C. for twenty minutes, poured over into ice water, crystals separated out therefrom were collected by filatration, washed with water, air dried and recrystallized from dimethyl formamide to give 2.6 grams (yield 80.0 percent) of the title compound. Melting point was 257° to 8° C. (with decomposition). Elementary analysis calculated as $C_{14}H_9ClFNO_3S$: C 51.46, H 2.78, N 4.29; Found: C 51.55, H 2.57, N 3.95.

Infrared absorption spectra (KBr, cm$^{-1}$): 1660, 1610, 1478, 1245, 1205.

Nuclear magnetic resonance spectra δ ($CF_3CO_2D$): 1.66 (3H, triplet, —$CH_2CH_3$), 4.82 (2H, quartet, —$CH_2CH_3$), 8.04 (1H, doublet, $C_2$—H), 8.38 (1H, doublet, $C_6$—H), 8.62 (1H, doublet, $C_9$—H), 8.92 (1H, doublet, $C_1$—H).

EXAMPLE 12

8-chloro-7-fluoro-5-oxo-5H-thiazolo(3,2-a)-quinoline-4-carboxylic acid

Ethyl 8-chloro-7-fluoro-5-oxo-5H-thiazolo(3,2-a)-quinoline-4-carboxylate(1.94 gram, 6 mmol) was suspended in a mixture of 6 ml of ethanol, 80 ml of water and 0.5 gram (12 mmol) of sodium hydroxide and the whole was heated to reflux for two hours. After cooled, the mixture was acidified with acetic acid, crystals separated therefrom were collected by filtration, washed with water, air dried, and recrystallized from dimethyl formamide to give the title compound. The yield was 1.3 grams (72.6 percent). Melting point was 310° to 15° C. (with decomposition). Elementary analysis calculated as $C_{12}H_5ClFNO_3S$: C 48.42, H 1.69, N 4.71; Found: C 48.44, H 1.48, N 4.40.

Infrared absorption spectra (KBr, cm$^{-1}$): 3125, 1690, 1595, 1490.

Nuclear magnetic resonance spectra δ ($CF_3CO_2D$): 8.05 (1H, doublet, $C_2$—H), 8.37 (1H, doublet, $C_8$—H), 8.63 (1H, doublet, $C_9$—H), 8.92 (1H, doublet, $C_1$—H).

EXAMPLE 13

7-fluoro-5-oxo-8(1-piperazinyl)-5H-thiazolo(3,2-a)quinoline-4-carboxylic acid

A mixture of 10.0 grams (0.034 mol) of 8-chloro-7-fluoro-5-oxo-5H-thiazolo(3,2-a)-quinoline-4-carboxylic acid, 29.0 grams (0.34 mol) of anhydrous piperazine and 250 ml of pyridine was heated to reflux for fifty-five hours. After cooled, the crystals separated out therefrom were collected by filtration, washed with pyridine and then with ether, the resulting crude crystals were suspended in 100 ml of water, then they were made dissolved therein by acidifying with acetic acid, treated with activated charcoal, adjusted to pH 7 with 2N sodium hydroxide solution, crystals separated out were collected by filtration, washed with water, dried, and recrystallized from dimethyl formamide to give the title compound. The yield was 4.78 grams (40.5 percent). Colorless crystals melting at 283° C. (with decomposition). Elementary analysis calculated as $C_{16}H_{14}FN_3O_3S$: C 55.32, H 4.06, N 12.10; Found: C 55.52, H 4.14, N 12.37.

Infrared absorption analysis (KBr, cm$^{-1}$): 1670, 1630, 1600, 1490, 1380, 1260.

Nuclear magnetic resonance spectra δ ($CF_3CO_2D$): 3.50–4.30

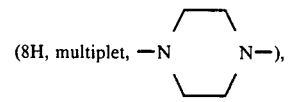

(8H, multiplet, —N    N—), 7.85 (1H, doublet, $C_9$—H), 7.96 (1H, doublet, $C_2$—H), 8.25 (1H, doublet, $C_6$—H), 8.96 (1H, doublet, $C_1$—H).

EXAMPLE 14

7-fluoro-8-(4-methyl-1-piperazinyl)-5-oxo-5H-thiazolo(3,2-a)-quinoline-4-carboxylic acid A mixture of 700 mg (2.35 mmol) of 8-chloro-7-fluoro-5-oxo-5H-thiazolo(3,2-a)-quinoline-4-carboxylic acid, 2.4 grams (23.5 mmol) of N-methylpiperazine and 30 ml of pyridine was heated to reflux for twelve hors in an oil bath. The content was concentrated under reduced pressure, water was added to the residue, insoluble matters therein were collected by filtration, washed with water, air dried and recrystallized from dimethyl formamide twice to give the title compound. The yield was 360 mg (42.4 percent). Melting point was 305° to 8° C. (with decomposition). Elementary analysis calculated as $C_{17}H_{16}FN_3O_3S$: C 56.50, H 4.46, N 11.63; Found: C 56.28, H 4.45, N 11.68.

Infrared absorption spectra (KBr, cm$^{-1}$): 1679, 1627, 1488, 1263.

Nuclear magnetic resonance spectra δ ($CF_3CO_2D$): 3.18 (3H, singlet, =$NCH_3$), 3.30–4.60

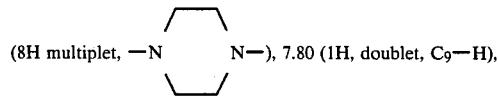

(8H multiplet, —N    N—), 7.80 (1H, doublet, $C_9$—H), 7.96 (1H, doublet, $C_2$—H, 8.24 (1H, doublet, $C_6$—H), 8.91 (1H, doublet, $C_1$—H).

EXAMPLE 15

8-(4-Allyl-1-piperazinyl)-7-fluoro-5-oxo-5H-thiazolo(3,2-a)-quinoline-4-carboxylic acid 7-fluoro-5-oxo-8-(1-piperazinyl)-5H-thiazolo-(3,2-a)-quinoline-4-carboxylic acid (400 mg., 1.2 mol) was dissolved in 5 ml of dimethyl formamide and heated at 70° C. for four hours after addition of 190 mg (1.4 mmol) of carbonic acid and 170 mg (1.4 mmol) of allyl bromide. The content was concentrated under reduced pressure and purified by column chromatography (using silica gel and chloroformmethanol)10:1)). Colorless crystals. The yield was 220 mg (68.8 percent). Melting point was 298° C. (with decomposition). Elementary analysis calculated as $C_{19}H_{18}FN_3O_3S$: C 58.23, H 4.76, N 10.72; Found: C 58.20- H 4.53, N 10.55.

Infrared absorption spectra (KBr, cm$^{-1}$): 1685, 1627, 1490, 1262, 1135, 1010.

Nuclear magentic resonance spectra δ (CF$_3$CO$_2$D): 3.00–4.60

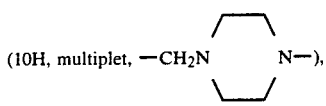

5.6–6.1 (3H multiplet, —CH=CH$_2$), 7.85 (1H, doublet, C$_9$—H), 7.98 (1H, doublet, C$_2$—H), 8.30 (1H, doublet, C$_6$—H), 8.97 (1H, doublet, C$_1$—H).

EXAMPLE 16

8-(4-ethyl-1-piperazinyl-7-fluoro-5-oxo-5H-thiazolo(3,2-a)-quinoline-4-carboxylic acid 7-fluoro-5-oxo-8-(1-piperazinyl)-5H-thiazolo(3,2-a)quinoline-4-carboxylic acid (300 mg. 0.86 mmol) was dissolved in 5 ml of dimethyl formamide and heated with stirring at 70° C. for twelve hours after addition of 142 mg (1.03 mmol) of potassium carbonate and 161 mg (1.03 mmol) of ethyl iodide. The content was concentrated under reduced pressure, water was added to the residue, crystals separated out therefrom were collected by filtration, washed with water, air dried, and recrystallized from dimethyl formamide to give the title compound. Colorless prisms. The yield was 130 mg (40.2 percent) and melting point was 307° to 10° C. (with decomposition). Elementary analysis calculated as C$_{18}$H$_{18}$FN$_3$O$_3$S: C 57.59, H 4.83, N 11.19; Found: C 57.59, H 4.83, N 10.92.

Infrared absorption spectra (KBr, cm$^{-1}$): 1680, 1630, 1490, 1262, 1030.

Nuclear magnetic resonance spectra δ (CF$_3$CO$_2$D): 1.55 (3H, triplet, —CH$_2$CH$_3$), 3.10–4.60

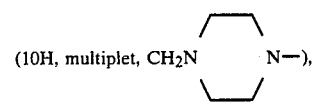

7.82 (1H, doublet, C$_9$—H), 8.29 (1H, doublet, C$_2$—H), 8.12 (1H, doublet, C$_6$—H), 8.92 (1H, doublet, C$_1$—H).

EXAMPLE 17

7-fluoro-8-(4-(2-hydroxyethyl)-1-piperazinyl)-5-oxo-5H thiazolo(3,2-a)-quinoline-4-carboxylic acid hydrobromide 7-fluoro-5-oxo-8-(1-piperazinyl)-5H-thiazolo(3,2-a)quinoline-4-carboxylic acid (350 mg) was suspended in 50 ml of dimethyl formamide, 150 mg of triethyl amine was added thereto, the mixture was stirred for thirty minutes at room temperature, and heated with stirring at twenty-two hours at 80° C. with 175 mg of ethylene bromohydrin. During the above reaction, each 120 mg of ethylene bromohydrin was added twice to the reaction solution. Then the reaction mixture was concentrated to about 20 ml under reduced pressure, crystals separated out therefrom were collected by filtration, washed with ethanol and dried to give 250 mg of the title compound as colorless powder. Melting point was 298° to 300° C. (with decomposition). Elementary analysis calculated as C$_{18}$H$_{18}$FN$_3$O$_4$S.HBr: C 45.77, H 4.05, N 8.90; Found: C 46.11, H 4.14, N 8.99.

Infrared absorption spectra (KBr, cm$^{-1}$): 3400, 2700, 2600, 2470, 1690, 1632, 1495, 1273, 1035, 1000, 940, 805, 795.

Nuclear magnetic resonance spectra δ (CF$_3$CO$_2$D): 3.20–4.65

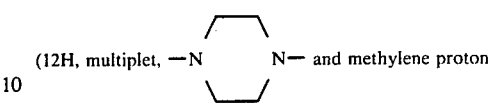

7.90 (1H, doublet, C$_9$—H), 7.97 (1H, doublet, C$_2$—H), 8.28 (1H, doublet, C$_6$—H), 9.00 (1H, doublet, C$_1$—H).

EXAMPLE 18

Ethyl 8-chloro-7-fluoro-1 methyl-5-oxo-5H-thiazolo(3,2-a)-quinoline-4-carboxylate A mixture of 6.02 grams (20 mmol) of ethyl 7-chloro-6-fluoro-4-hydroxy-2-mercaptoquinoline-3-carboxylate and 2.04 grams (22.0 mmol) of 1-chloro-2-oxopropane in 300 ml of ethanol was heated to reflux for twenty-four hours. This was concentrated to 20 ml under reduced pressure, allowed to stand at room temperature, crystals*separated out therefrom were collected by filtration, and washed with n-hexane to give 5.74 grams of crystalline substance. This was stirred for one hour at room temperature with 15 ml of concentrated sulfuric acid. The reaction solution was poured over into ice flakes, crystals separated out were collected by filtration, washed with water, dried and recrystallized from dimethyl formamide to give 4.86 grams (yield 71.7 percent) of ethyl 8-chloro-7-fluoro-1-methyl-5-oxo-5H-thiazolo(3,2-a)-quinoline-4-carboxylate. (*The crystals were a mixture of ring closed compound and ring unclosed one, and the latter was not isolated at this time). Melting point was 291° to 293° C. (with decomposition). Elementary analysis calculated as C$_{15}$H$_{11}$ClFNO$_3$S: C 53,03, H 3.26, N 4.12; Found: C 52.47, H 3.47, N 4.57.

Infrared absorption spectra (KBr, cm$^{-1}$): 1695, 1670, 1605, 1310, 800.

Nuclear magnetic resonance spectra δ (CF$_3$CO$_2$D): 1.66 (3H, triplet, OCH$_2$CH$_3$), 3.23 (3H singlet, C$_1$—CH$_3$), 4.80 (2H, quartet, OCH$_2$CH$_3$), 7.66 (1H, singlet, C$_2$—H), 8.39 (1H, doublet, C$_6$—H), 8.93 (1H, doublet, C$_9$—H).

EXAMPLE 19

8-chloro-7-fluoro-1-methyl-5-oxo-5H-triazolo(3,2-a)quinoline-4-carboxylic acid

Ethyl 8-chloro-7-fluoro-1-methyl-5-oxo-5H thiazolo(3,2-a)quinoline-4-carboxylate (10.0 grams, 29.4 mmol) was suspended in 40 ml of ethanol, then 3.88 grams of potassium hydroxide and 380 ml of water were added thereto, and the mixture was heated to reflux for six hours with stirring. Then it was concentrated to 300 ml under reduced pressure, neutralized with acetic acid, vigorously stirred overnight, crystals separated out therefrom were collected by filtration, washed with water, dried and recrystallized from dimethyl formamide to give 8.08 grams of the title compound. The yield was 88.1 percent. Melting point was 317° to 319° C. (with decomposition). Elementary analysis calculated was C$_{13}$H$_7$ClFNO$_3$S: C 50.09, H 2.26, N 4.49; Found: C 50.32, H 2.37, N 4.37.

Infrared absorption spectra (KBr, cm$^{-1}$): 1695, 1590, 1050, 805, 800.

Nuclear magnetic resonance spectra δ (CF$_3$CO$_2$D): 3.26 (3H, singlet, C$_1$—CH$_3$), 7.72 (1H, singlet, C$_2$—H), 8.46 (1H, doublet, C$_6$—H), 8.98 (1H, doublet, C$_9$—H).

EXAMPLE 20

7,8-difluoro-1-methyl-5-oxo-5H-thiazolo(3,2-a)quinoline-4-carboxylic acid

Ethyl 7,6-difluoro-4-hydroxy-2-mercaptoquinoline-3-carboxylate (2.85 grams, 0.01 mol) and 1.02 grams (0.011 mol) of chloroacetone were dissolved in 30 ml of ethanol and the mixture was heated to reflux for sixteen hours. After cooled, the crystals separated out therefrom were collected by filtration and washed with ether to give 2.50 grams of crude crystals. The crystals were added to 15 grams of concentrated sulfuric acid with ice cooling, the mixture was stirred for one hour, and stirred for another thirty minutes at room temperature. The reaction solution was poured over into ice water, crystals separated out were collected by filtration, washed with water, then with ether, and dried with air to give 2.11 grams of 7,8-difluoro-1-methyl-5-oxo-5H-thiazolo(3,2-a)-quinoline-4-carboxylic acid. This was recrystallized from a mixture of dimethyl formamide and ethanol to give the product which melted at 270° to 80° C. (with decomposition). Elementary analysis calculated as C$_{13}$H$_7$FNO$_3$S: C 52.88, H 2.39, N 4.74; Found: C 53.05, H 2.40, N 4.61.

Infrared absorption spectra (KBr, cm$^{-1}$): 1690, 1610, 1595, 1550.

Nuclear magnetic resonance spectra δ (CF$_3$CO$_2$D): 3.25 (3H, singlet, C$_1$—H), 7.68 (1H, singlet, C$_2$—H), 8.52 (1H, triplet, C$_9$—H), 8.71 (1H, double doublet, C$_6$—H).

EXAMPLE 21

7-fluoro-1-methyl-5-oxo-8-(1-piperazinyl)-5H-thiazolo(3,2-a)-quinoline-4-carboxylic acid (a) 8-chloro-7-fluoro-1-methyl-5-oxo-5H-thiazolo(3-2-a)-quinoline 4-carboxylic acid (15.0 grams, 4.81 mmol) was heated to reflux in a mixture of 4.14 grams (48.1 mmol) of anhydrous piperazine and 28 ml of pyridine for twenty hours. After the reaction was completed, the mixture was allowed to stand at room temperature, crystals separated out therefrom were collected by filtration, washed with an aqueous acetic acid, then dissolved in aqueous 10 percent solution of sodium hydroxide, adjusted to pH 7.2 with aqueous solution of acetic acid, crystals separated out were collected by filtration, washed with water, dried, and recrystallized from dimethyl formamide to give 220 mg of the title compound. The yield was 12.7 percent and melting point was 284° to 6° C. (decomposition). Elementary analysis calculated as C$_{17}$H$_{16}$FN$_3$O$_3$·½H$_2$O: C 55.13, H 4.63, N 11.34; Found: C 55.63, H 4.61, N 11.34.

Infrared absorption spectra (KBr, cm$^{-1}$): 3200 to 3600, 1700, 1635, 805.

Nuclear magnetic resonance spectra δ (CF$_3$CO$_2$D): 3.25 (3H, singlet, C$_1$—CH$_3$), 3.2–4.4

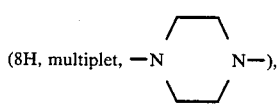
(8H, multiplet, —N N—), 7.71 (1H, singlet, C$_2$—H), 8.1 to 8.6 (2H, multiplet, C$_6$—H, C$_9$—H).

b. To a mixture of 295 mg (1 mmol) of 7,8-difluoro-1-methyl-5-oxo-5H-thiazolo(3,2-a)-quinoline-4-carboxylic acid and 344 mg (4 mmol) of anhydrous piperazine was added 2 ml of pyridine and the whole was heated with stirring for 2 hours in an oil bath kept at 100° C. After cooled, crystals separated out therefrom were collected by filtration, and washed with ethanol to give 322 mg of crude crystals. Those were recrystallized from a mixture of dimethyl formamide and ethaanol to give 264 mg of the title compound. The yield was 73 percent. Melting point was 284° to 6° C. (with decomposition). The resulting compound was identified with that obtained in the method (a) by infrared absorption spectra and nuclear magnetic resonance spectra.

EXAMPLE 22

7-fluoro-1-methyl-8-(4-methyl-1-piperazinyl)-5-oxo-5H-thiazolo(3,2-a)-quinoline-4-carboxylic acid and 8-chloro-1-methyl-7-(4-methyl-1-piperazinyl)-5-oxo-5H-thiazolo(3,2-a)-quinoline-4-carboxylic acid (a) Five grams (16.0 mmol) of 8-chloro-7-fluoro-1-methyl-5-oxo-5H-thiazolo(3,2-a)-quinoline-4-carboxylic acid was heated to reflux for twenty-four hours in a mixture of 8.0 grams (80 mmol) of N-methylpiperazine and 150 ml of pyridine and the refluxing was continued for more than thirty hours after addition of 8.0 grams (80 mmol) more of N-methylpiperazine. Pyridine was removed therefrom under reduced pressure, ethyl acetate was added thereto, crystalline substance appeared was collected by filtration, and subjected to a silica gel column chromatography. The column was eluted with a mixture (10:1) of chloroform and methanol and from the first eluate was obtained 1.83 grams of title 8-chloro-1-methyl-7-(4-methyl-1-piperazinyl)-5-oxo-5H-thiazolo(3,2-a)-quinoline-4-carboxylic acid. The yield was 26.1 percent. Melting point was 291° to 293° C. (with decomposition). Elementary analysis calculated as C$_{18}$H$_{18}$ClN$_3$O$_3$S: C 55.17, H 4.63, N 10.72; Found: C 55.11, H 4.70, N 10.63.

Infrared absorption spectra (KBr, cm$^{-1}$): 1690, 1590, 805.

Nuclear magnetic resonance spectra δ (CF$_3$CO$_2$D): 3.22 (6H, wide singlet, C$_1$—CH$_3$, =N—CH$_3$), 3.3 to 4.2

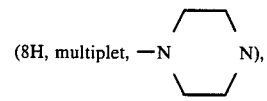
(8H, multiplet, —N N), 7.68 1H, singlet, C$_2$—H), 8.29 (1H, singlet, C$_6$—H), 8.96 (1H, singlet, C$_9$—H).

From the succeeding eluate was obtained 2.06 grams (yield 34.2 percent) of 7-fluoro-1-methyl-8-(4-methyl-1-piperazinyl)-5-oxo-5H-thiazolo(3,2-a)-quinoline-4-carboxylic acid. Melting point 288° to 290° C. (with decomposition). Elementary analysis calculated as C$_{18}$H$_{18}$FN$_3$O$_3$S: C 57.59, H 4.83, N 11.19; Found: C 57.42, H 4.98, N 11.03.

Infrared absorption spectra (KBr, cm$^{-1}$): 1695, 1630, 800.

Nuclear magnetic resonance spectra δ (CF$_3$CO$_2$D): 3.22 (3H, singlet, —NCH$_3$), 3.27 (3H, singlet, C$_1$—CH$_3$), 3.3 to 4.4

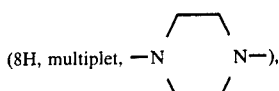
(8H, multiplet, —N N—), 7.70 (1H, singlet, $C_2$—H), 8.33 (1H, doublet, $C_9$—H), 8.45 (1H, doublet, $C_6$—H).

b. To a mixture of 295 mg (1 mmol) of 7,6-difluoro-1-methyl-5-oxo-5H-thiazolo(3,2-a)-quinoline-4-carboxylic acid and 400 mg (4 mmol) of N-methylpiperazine was added 2 ml of pyridine and the whole mixture was heated with stirring for two hours in an oil bath of 100° C. After cooled, crystals separated out therefrom were collected by filtration and washed with ethanol to give 364 mg of crude crystals. Those were recrystallized from a mixture of dimethylformamide and ethanol to give 284 mg (yield 76 percent) of the title 7-fluoro-1-methyl-8-(4-methyl-1-piperazinyl)-5-oxo-5H-thiazolo(3,2-a)-quinoline-4-carboxylic acid. Melting point was 285° to 7° C. (with decomposition). This was identified with the compound obtained in the previous method (a) by measurement of infrared absorption spectra and nuclear magnetic resonance spectra.

EXAMPLE 23

8-(4-Allyl-1-piperazinyl)-7-fluoro-1-methyl-5-oxo-5H-thiazolo(3,2-a)-quinoline-4-carboxylic acid and 7-(4-allyl-1-piperazinyl)-8-chloro-1-methyl-5-oxo-5H-thiazolo(3,2- a)-quinoline-4-carboxylic acid A mixture of 1.0 gram (3.2 mmol) of 8-chloro-7-fluoro-1-methyl-5-oxo-5H-thiazolo(3,2-a)-quinoline-4-carboxylic acid, 2.0 grams (16 mmol) of N-allyl piperazine, and 50 ml of pyridine was heated to reflux for seventy-two hours. The content was concentrated, water was added to the residue, insoluble matter was collected by filtration, washed with water, dried with air, and the resulting crystals obtained by further filtration was purified by a column chromatography using silica gel and a 1:20 mixture of methanol and chloroform. From the firstly eluted fraction was obtained 7-(4-allyl-1-piperazinyl)-8-chloro-1-methyl-5-oxo-5H-thiazolo(3,2-a)-quinoline-4-carboxylic acid. Colorless crystals. The yield was 480 mg (35.8 percent). Melting point was 267° to 268° C. (with decomposition). Elementary analysis calculated: C 57.48, H 4.82, N 10.05; Found: 57.02, H 4.68, N 9.79.

Infrared absorption spectra (KBr, cm$^{-1}$): 1690, 1575, 1470, 1010, 810.

Nuclear magnetic resonance spectra δ(CF$_3$CO$_2$D): 3.00 to 4.30

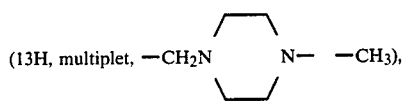
(13H, multiplet, —CH$_2$N N— —CH$_3$), 5.6 to 6.1 (3H, multiplet, —CH=CH$_2$), 7.70 (1H, singlet, $C_2$—H), 8.30 (1H, singlet, $C_6$—H), 8.95 (1H, singlet, $C_9$—H).

From the next eluted fraction was obtained 8-(4-allyl-1-piperazinyl)-7-fluoro-1-methyl-5-oxo-5H-thiazolo(3,2-a)-quinoline-4-carboxylic acid. Colorless crystals. The yield was 510 mg (39.8 percent). Melting point was 225° to 6° C. (with decomposition). Elementary analysis calculated: C 57.26, H 5.29, N 10.02; Found: C 57.17, H 5.43, N 9.74.

Infrared absorption spectra (KBr, cm$^{-1}$): 1680, 1630, 1490, 1270.

Nuclear magnetic resonance spectra δ(CF$_3$CO$_2$D): 3.23 (3H, singlet, —CH$_3$), 3.30 to 4.50

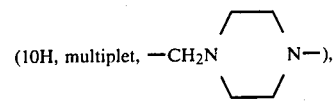
(10H, multiplet, —CH$_2$N N—), 5.6 to 6.0 (3H, multiplet, —CH=CH$_2$), 7.61 (1H, singlet, $C_2$—H), 8.21 (1H, doublet, $C_9$—H), 8.31 (1H, doublet, $C_6$—H).

EXAMPLE 24

7-fluoro-1-methyl-5-oxo-8-4-(thiomorpholino)-5H-thiazolo(3,2-a)-quinoline-4-carboxylic acid A mixture of 295 mg (1 mmol) of 7,8-difluoro-1-methyl-5-oxo-5H-thiazolo(3,2-a)quinoline 4-carboxylic acid and 412 mg (4 mmol) of thiomorpholine was added to 2 ml of pyridine and the whole mixture was heated with stirring for five hours in an oil bath kept at 80° C. After cooled, crystals separated out therefrom were collected by filtration, washed with ethanol, and the resulting crude crystals were recrystallized from dimethylformamide to give 272 mg of 7-fluoro-1-methyl-5-oxo-8-(4-thiomorpholino)-5H-thiazolo(3,2-a)-quinoline-4-carboxylic acid. Melting point was 318° to 320° C. (with decomposition). Elementary analysis calculated as C$_{17}$H$_{15}$FN$_2$O$_3$S: C 53.95, H 4.00, N 7.40; Found: C 53.63, H 4.04, N 7.19.

Infrared absorption spectra (KBr, cm$^{-1}$): 1695, 1630, 1575, 1490, 1450, 1260, 965, 805, 795.

Nuclear magnetic resonance spectra δ(CF$_3$CO$_2$D): 3.25 (3H, singlet, $C_1$—CH$_3$), 3.00 to 3.50 (4H, multiplet, $C'_6$—H$_2$ and $C'_2$—H$_2$ of thiomorpholino group), 4.00 to 4.50 (4H, multiplet, $C'_5$—H$_2$ and $C'_3$—H$_2$ of thiomorpholino group), 7.70 (1H, singlet, $C_2$—H), 8.57 (1H, doublet, $C_6$—H), 8.00 (1H, doublet, $C_9$—H).

EXAMPLE 25

8-ethoxy-7-fluoro-1-methyl-5-oxo-5H-thiazolo(3,2-a)quinoline 4-carboxylic acid 7,8-Difluoro-1-methyl-5-oxo-5H-thiazolo(3,2-a)-quinoline-4-carboxylic acid (295 mg, 1 mmol) was suspended in ethanol and sodium ethoxide solution (prepared from 5 ml of anhydrous ethanol and 57 mg of metal sodium) was dropped therein with stirring at room temperature. The mixture was stirred for one hour at room temperature and heated to reflux for 2 hours more. Ethanol was evaporated therefrom, the residue was dissolved in water, acidified with acetic acid, crystals separated therefrom were collected by filtration, and washed with water to give 290 mg of crude crystals. Those were recrystallized from dimethyl formamide to give 230 mg of 8-ethoxy-7-fluoro-1-methyl-5-oxo-5H-thiazolo(3,2-a)-quinoline-4-carboxylic acid. Melting point was 273° to 5° C. (with decomposition). Elementary analysis calculated as C$_{15}$H$_{12}$FNO$_4$S: C 56.07, H 3.76, N 4.36; Found: C 56.51, H 3.70, N 4.44.

Infrared absorption spectra (KBr, cm$^{-1}$): 3400 to 2400, 1690, 1630, 1590, 1480, 1365, 1275, 1250, 1050, 1030, 935, 810.

Nuclear magnetic resonance spectra δ(CF₃CO₂D): 1.68 (3H, triplet, —OCH₂CH₃), 3.29 (3H, singlet, C₁—CH₃), 4.47 (2H, quartet-OCH₂CH₃), 7.67 (1H, singlet, C₂—H), 8.35 (1H, doublet, C₉—H), 8.37 (1H, doublet, C₆—H).

EXAMPLE 26

Ethyl 8-chloro-1-ethyl-7-fluoro-5-oxo-5H-thiazolo(3,2-a)-quinoline-4-carboxylate (a) To 3.0 grams (10 mmol) of ethyl 7-chloro-6-fluoro-4-hydroxy-2-mercaptoquinoline-3-carboxylate were added 1.7 grams (11.5 mmol) of bromethyl ethyl ketone and 100 ml of ethanol and the mixture was heated to reflux for one hour. Ethanol was removed therefrom under reduced pressure and the residue was recrystallized from ethanol to give 3.2 grams of ethyl 7-chloro-6-fluoro-4-hydroxy-2-(2-oxo-1-butanethio)-quinoline-3-carboxylate. The yield was 86 percent. Melting point was 239° to 242° C. (with decomposition). Elementary analysis calculated as C₁₆H₁₅ClFNO₄S: C 51.69, H 4.07, N, 3.77; Found: C 51.52, H. 4.41, N. 3.56.

Infrared absorption spectra (KBr, cm⁻¹): 1700, 1595, 1480, 1045.

Nuclear magnetic resonance spectra δ(CF₃CO₂D): 1.15 (triplet, CH₂CH₃), 1.40 (3H, triplet, CH₂CH₃), 2.20 to 2.80 (2H, multiplet, —SCH₂), 3.15 to 4.36 (4H, multiplet, —CH₂CH₃×2), 8.23 (1H, doublet, C₅—H), 9.05 (1H, doublet, C₈—H).

b. to 1.84 grams (4.95 mmol) of ethyl 7-chloro-6-fluoro-4-hydroxy-2-(2-ozo-1-butylthio)-quinoline-3-carboxylate was added 7.0 grams of sulfuric acid and the mixture was heated with stirring at 70° C. for fifteen minutes. After cooled with ice, 20 grams of ice was added thereto, the mixture was stirred for ten minutes, crystals separated out therefrom were collected by filtration, washed with water, dried and recrystallized from ethanol to give 1.5 grams of ethyl 8-chloro-1-ethyl-7-fluoro-5-oxo-5H-thiazolo(3,2-a)-quinoline-4-carboxylate. The yield was 86 percent. Melting point was 260° to 262° C. (with decomposition). Elementary analysis calculated as C₁₆H₁₃ClFNO₃S: C 54.32, H 3.70, N 3.96; Found: C 54.52, H 3.95, N 3.65.

Infrared absorption spectra (KBr, cm⁻¹): 1690, 1585, 1503, 1470.

Nuclear magnetic resonance spectra δ(CF₃CO₂D): 1.70 (3H, triplet, CH₂CH₃), 1.72 (3H, triplet, —CH₂CH₃), 3.64 (2H, quartet, CH₂CH₃, 4.82 (2H, quartet, —CH₂CH₃), 7.75 (1H, singlet, C₂—H), 8.42 (1H, doublet, C₆—H), 8.94 (1H, doublet, C₉—H).

EXAMPLE 27

8-chloro-1-ethyl-7-fluoro-5-oxo-5H-thiazolo(3,2-a)quinoline-4-carboxylic acid

To 1.5 grams (4.24 mmol) of ethyl 8-chloro-1-ethyl-7-fluoro-5-oxo-5H-thiazolo(3,2-a)-quinoline-4-carboxylate were added 1.2 grams of potassium hydroxide, 100 ml of water and 100 ml of ethanol and the mixture was heated to reflux for one hour. Ethanol was removed therefrom under reduced pressure, acetic acid was added to the residue, crystals separated out therefrom on acidification were collected by filtration, washed with water, dried and recrystallized from dimethyl formamide to give 1.25 grams of 8-chloro-1-ethyl-7-fluoro-5-oxo-thiazolo (3,2-a)quinoline 4-carboxylic acid. The yield was 91 percent. Melting point was 274° to 5° C. (with decomposition). Elementary analysis calculated as C₁₄H₁₉ClFNO₃S: C 51.62, H 5.88, N 4.30; Found: C 51.59; H 6.21, N 4.51.

Infrared absorption spectra (KBr, cm⁻¹): 2700 to 2000, 1690, 1584, 1470.

Nuclear magnetic resonance spectra δ(CF₃CO₂D): 1.71 (3H, triplet, —CH₂CH₃), 3.62 (2H, quartet, —CH₂CH₃), 3.62 (2H, quartet, —CH₂CH₃), 7.76 (1H, singlet, C₂—H), 8.43 (1H, doublet, C₆—H), 8.94 (1H, doublet, C₉—H).

EXAMPLE 28

1-ethyl-7-fluoro-5-oxo-8-(1-piperazinyl)-5H-thiazolo (3,2-a)-quinoline-4-carboxylic acid One gram (3.1 mmol) of 8-chloro-1-ethyl-7-fluoro-5-oxo-5H-thiazolo(3,2-a)-quinoline-4-carboxylic acid was heated to reflux for fifty-two hours in a mixture of 2.7 grams (31.0 mmol) of anhydrous piperazine and 50 ml of pyridine. After the reaction was completed, the mixture was allowed to cool to room temperature, crystals separated out therefrom were collected by filtration, washed with ether, purified by silica gel chromatography, and recrystallized from dimethyl formamide to give 140 mg of the title product. The yield was 12 percent. Melting point was 247° to 251° C. Elementary analysis calculated as C₁₈H₁₈FN₃O₃S: C 57.59, H 4.83, N 11.19; Found: C 57.42, H 4.99, N 11.08.

Infrared absorption spectra (KBr, cm⁻¹): 2700 to 2000, 1680, 1630, 1590, 1490.

Nuclear magnetic resonance spectra δ(CF₃CO₂D): 1.68 (3H, triplet, —OCH₂CH₃), 3.00 to 4.47

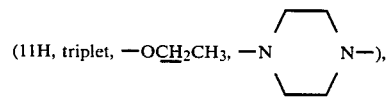

(11H, triplet, —OCH₂CH₃, —N    N—), 7.71 (1H, singlet, C₂—H), 8.18 (1H, doublet, C₉—H), 8.37 (1H, doublet, C₆—H).

EXAMPLE 29

1-ethyl-7-fluoro-8-(4-methyl-1-piperazinyl)-5-oxo-5H-thiazolo(3,2-a)-quinoline-4-carboxylic acid To 1.0 gram (3.07 mmol) of 8-chloro-1-ethyl-7-fluoro-5-oxo-5H-thiazolo(3,2-a)quinoline 4-carboxylic acid were added 3.1 grams of N-methyl piperazine and 100 ml of pyridine and the mixture was heated to reflux for forty-two hours. Pyridine was evaporated therefrom under reduced pressure, the residue was washed with ether, purified by silica gel chromatography, and recrystallized from dimethyl formamide to give 337 mg of the title compound. The yield was 28 percent. Melting point was 252° to 255° C. (with decomposition). Elementary analysis calculated as C₁₉H₂₀FN₃O₃S: C 58.60, H 5.18, N 10.79; Found: C 58.43, H 5.20, N 10.52.

Infrared absorption spectra (KBr, cm⁻¹): 1710, 1630, 1590, 1530, 1485.

Nuclear magnetic resonance δ(CF₃CO₂D): 1.68 (3H, triplet, —OCH₂CH₃), 3.32 (3H, singlet, NCH₃), 3.00 to 4.47

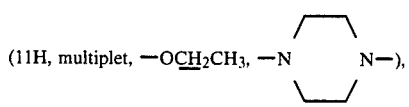

(11H, multiplet, —OCH₂CH₃, —N    N—), 7.71 (1H, singlet, $C_2$—H), 8.18 (1H, doublet, $C_9$—H), 8.37 (1H, doublet, $C_6$—H).

EXAMPLE 30

Ethyl 8-chloro-1-ethoxycarbonylmethyl-7-fluoro-5-oxo-5H-thiazolo(3,2-a)-quinoline-4-carboxylate (a) To 3.0 grams (10 mmol) of ethyl 7-chloro-6-fluoro-4-hydroxy-2-mercaptoquinoline-3-carboxylate was added a solution of 0.25 gram (10.87 mmol) of sodium in 100 ml of ethanol. The mixture was stirred for about twenty minutes, then 1.96 grams (11.91 mmol) of ethyl 4-chloroacetoacetate was added thereto, and the mixture was stirred at room temperature for twelve hours. Ethanol was evaporated therefrom under reduced pressure, 100 ml of water was added to the residue, crystals appeared and were thereby collected by filtration, and recrystallized from ethanol to give 3.85 grams of ethyl 7-chloro-2-(3-ethoxycarbonyl-2-oxo-propylthio)-6-fluoro-4-hydroxyquinoline-3-carboxylate. The yield was 86 percent. Melting point was 167° to 170° C. Elementary analysis calculated as $C_{18}H_{17}ClFNO_6S$: C 50.30, H 3.90, N 3.26: Found: C 50.51, H 4.15, N 3.42.

Infrared absorption spectra (KBr, cm$^{-1}$): 3170, 1735, 1670, 1596, 1465.

Nuclear magnetic resonance spectra $\delta(CF_3CO_2D)$: 1.15 (3H, —OCH$_2$CH$_3$), 1.39 (3H, triplet, —OCH$_2$CH$_3$), 3.24 (2H, singlet, —CO—CH$_2$CO$_2$—), 4.35 (2H, singlet, —SCH$_2$CO), 4.39 (2H, quartet, —OCH$_2$CH$_3$), 4.84 (2H, quartet, —OCH$_2$CH$_3$), 8.21 (1H, doublet, C$_5$—H), 9.20 (1H, doublet, C$_8$—H).

b. To 2.0 grams (4.65 mmol) of ethyl 7-chloro-2-(3-ethoxycarbonyl-2-oxopropylthio)-6-fluoro-4-hydroxyquinoline-3-carboxylate was added 10 grams of sulfuric acid and the mixture was heated with stirring at 70° C. for about twenty minutes. This was cooled to room temperature, then 20 grams of ice was added thereto, crystals separated out therefrom were collected by filtration, washed with water, dried and recrystallized from ethanol to give ethyl-8-chloro-1-(ethoxycarbonylmethyl)-7-fluoro-5-oxo-5H-thiazolo(3,2-a)-quinoline-4-carboxylate. The yield was 1.66 grams (86 percent). Melting point was 214° to 218° C. (with decomposition). Elementary analysis calculated as $C_{18}H_{15}ClFNO_5S$: C 52.50, H 3.67, N 3.40; Found: C 52.59, H 3.91, N 3.62.

Infrared absorption spectra (KBr, cm$^{-1}$): 1730, 1661, 1630, 1608, 1460.

Nuclear magnetic resonance spectra $\delta(CF_3CO_2D)$: 1.45 (3H, triplet, —OCH$_2$CH$_3$), 1.74 (3H, triplet, —OCH$_2$CH$_3$), 4.42 (2H, quartet, —OCH$_2$CH$_3$), 4.35 (2H, singlet, —CH$_2$CO$_2$—), 4.90 (2H, quartet, —OCH$_2$CH$_3$), 8.00 (1H, singlet, C$_2$—H), 8.56 (1H, doublet, C$_9$—H), 8.57 (1H, doublet, C$_6$—H).

EXAMPLE 31

1-carboxymethyl-8-chloro-7-fluoro-5-oxo-5H-thiazolo(3,2-a)-quinoline-4-carboxylic acid To 1.5 grams (3.64 mmol) of ethyl 8-chloro-1-(ethoxycarbonylmethyl)-7-fluoro-5-oxo-5H-thiazolo (3,2-a)quinoline 4-carboxylate were added 1.0 gram (18.21 mmol) of potassium hydroxide, 10 ml of water and 100 ml of ethanol and the mixture was heated to reflux for four hours. Ethanol was evaporated therefrom under reduced pressure, 20 ml of water was added to the residue so that the residue was dissolved therein, then acidified with acetic acid with stirring and ice cooling, crystals separated out therefrom were collected by filtration, washed with water, dried and recrystallized from dimethyl formamide to give 1.21 grams of 8-chloro-1-(carboxymethyl)-7-fluoro-5-oxo-5H-thiazolo(3,2-a)-quinoline-4-carboxylic acid. The yield was 94 percent. Melting point was 236° to 238° C. (with decomposition). Elementary analysis calculated as $C_{14}H_{17}ClFNO_5S$: C 47.27, H 4.82, N. 3.94; Found: C 47.41, H 4.91, N 4.01.

Infrared absorption spectra (KBr, cm$^{-1}$): 1715, 1685, 1615, 1590, 1480.

Nuclear magnetic resonance spectra $\delta(CF_3CO_2D)$: 4.85 (2H, singlet, —CH$_2$CO$_2$H), 8.05 (1H, singlet, C$_2$—H), 8.36 (1H, singlet, C$_9$—H), 8.68 (1H, singlet, C$_6$—H).

EXAMPLE 32

1-Carboxymethyl-7-fluoro-8-(4-methyl-1-piperazinyl)-5-oxo-5H-thiazolo(3,2-a)-quinoline-4-carboxylic acid To 1.0 gram (2.81 mmol) of 8-chloro-1-(carboxymethyl)-7-fluoro-5-oxo-5H-thiazoloe(3,2-a)-quinoline-4-carboxylic acid were added 2.8 grams (28.10 mmol) of N-methyl piperazine and 40 ml of pyridine and the mixture was heated to reflux for forty-eight hours. Pyridine was evaporated therefrom under reduced pressure, ether was added to the residue, the mixture was washed, then washed with a small amount of ethanol, dried, purified by silica gel column chromatography, and recrystallized from dimethyl formamide to give 420 mg of the title compound. The yield was 36 percent. Melting point was 286° to 288° C. (with decomposition). Elementary analysis calculated as $C_{19}H_{18}FN_3O_5S$: C 54.41, H 4.33, N 10.02; Found: C 54.72, H 4.18, N 10.16.

Infrared absorption spectra (KBr, cm$^{-1}$): 2700 to 2000, 1690, 1630, 1490, 1450.

Nuclear magnetic resonance spectra $\delta(CF_3CO_2D)$: 3.25 (3H, singlet, NCH$_3$), 3.30 (2H, singlet, CH$_2$CO$_2$H), 3.45 to 4.40 (8H, multiplet, —N N—), 7.65 (1H, singlet, C$_2$—H), 8.25 (1H, doublet, C$_9$—H), 8.36 (1H, doublet, C$_6$—H).

EXAMPLE 33

Ethyl 8-chloro-1-(2-ethoxycarbonylethyl)-7-fluoro-5-oxo-5H-thiazolo(3,2-a)-quinoline-4-carboxylate (a) A solution prepared from 0.38 gram (16.6 mmol) of sodium and 200 ml of ethanol was added to five grams (16.6 mmol) of ethyl 7-chloro-6-fluoro-4-hydroxy-2-mercaptoquinoline-3-carboxylate and the mixture was stirred at room temperature for about twenty minutes. The mixture was stirred for an additional four hours at room temperature after the addition of 3.3 grams (18.2 mmol) of ethyl 8-chloro-gamm-oxo-valerate. Ethanol was evaporated therefrom under reduced pressure, water was added to the residue, crystals were collected therefrom by filtration, washed with water, dried and recrystallized from ethanol to give 6.6 grams of ethyl 7-chloro-2-(4-ethoxycarbonyl-2-oxo-1-butylthio)-6-fluoro-4-hydroxyquinoline-3-carboxylate. The yield was 90 percent. Melting point was 144.4° C. Elementary analysis calculated as $C_{19}H_{19}ClFNO_6S$: C 51.41, H 4.32, N 3.16; Found: C 51.62, H 4.39, N 3.29.

Infrared absorption spectra (KBr, cm$^{-1}$): 3240, 1742, 1676, 1591, 1570, 1485.

Nuclear magnetic resonance spectra $\delta(CF_3CO_2D)$: 1.45 (3H, triplet, —OCH$_2$CH$_3$), 1.64 (3H, triplet, —OCH$_2$CH$_3$), 2.50 to 3.36 (4H, wide singlet, —CH$_2$CH$_2$—), 3.95 (2H, singlet, —SCH$_2$CO—), 4.37 (2H, quartet, —OCH₂CH₃), 4.75 (2H, quartet, —OCH₂CH₃), 8.22 (1H, doublet, C₈—H), 9.16 (1H, doublet, C₅—H).

b. To 6.0 grams (13.52 mmol) of ethyl 7-chloro-2-(4-ethoxycarbonyl-2-oxo-1-butylthio)-6-fluoro-4-hydroxyquinoline-3-carboxylate was added 30 grams of sulfuric acid. The mixture was stirred at room temperature for about thirty minutes and then heated at 70° C. for about twenty minutes with stirring. After cooled, 100 grams of ice was added thereto, crystals separated out therefrom were collected by filtration, washed with water, dried and recrystallized from ethanol to give 5.30 grams of ethyl 8-chloro-1-(2-ethoxycarbonylethyl)-7-fluoro-5-oxo-5H-thiazolo(3,2-a)-quinoline-4-carboxylate. The yield was 92 percent. Melting point was 200.0° C. Elementary analysis calculated as C₁₉H₁₇ClFNO₅S: C 53.59; H 4.02, N 3.29; Found: C 53.51, H 4.40, N 3.49.

Infrared absorption spectra (KBr, cm⁻¹): 1730, 1660, 1635, 1612, 1460.

Nuclear magnetic resonance spectra δ(CF₃CO₂D): 1.42 (3H, triplet, —OCH₂CH₃), 1.70 (3H, triplet, —OCH₂CH₃), 3.21 (2H, triplet, —CH₂CH₂), 4.04 (3H, triplet, —CH₂CH₂), 4.39 (2H, quartet, —OCH₂CH₃), 4.84 (2H, quartet, —OCH₂CH₃), 7.82 (1H, singlet, C₂—H), 8.48 (1H, doublet, C₆—H).

EXAMPLE 34

1-(2-carboxyethyl)-8-chloro-7-fluoro-5-oxo-5H-thiazolo(3,2-a)-quinoline-4-carboxylic acid.

To 4.2 grams (9.86 mmol) of ethyl 8-chloro-1-(2-ethoxycarbonyl-ethyl)-7-fluoro-5-oxo-5H-thiazolo(3,2-a)-quinoline-4-carboxylate were added 3.9 grams (69.02 mmol) of potassium hydroxide, 100 ml of water and 100 ml of ethanol and the mixture was heated to reflux for four hours. Ethanol was evaporated therefrom under reduced pressure and the residue was acidified with acetic acid. Crystals separated out therefrom were collected by filtration, washed with water, dried and recrystallized from dimethyl formamide to give 3.29 grams of 1-(2-carboxy-ethyl)-8-chloro-7-fluoro-5-oxo-5H-thiazolo(3,2-a)-quinoline-4-carboxylic acid. The yield was 90 percent. Melting point was 298° to 301° C. (with decomposition). Elementary analysis calculated as C₁₅H₁₉ClFNO₅S: C 48.73, H 5.18, N 3.79; Found: C 48.91, H 5.24, N 3.81.

Infrared absorption spectra (KBr, cm⁻¹): 2700 to 2000, 1730, 1680, 1530, 1440.

Nuclear magnetic resonance spectra δ(CF₃CO₂D): 3.20 (2H, triplet, —CH₂CH₂—), 3.95 (2H, triplet, —CH₂CH₂—), 7.84 (1H, singlet, C₂—H), 8.50 (1H, doublet, C₆—H), 8.86 (1H, doublet, C₉—H).

EXAMPLE 35

(1-(2-carboxyethyl)-7-fluoro-8-(4-methyl-1-piperazinyl)-5-oxo-5H-thiazolo(3,2-a)-quinoline-4-carboxylic acid To one gram (2.705 mmol) of 1-(2-carboxymethyl)-8-chloro-7-fluoro-5-oxo-5H-thiazolo(3,2-a)quinoline 4-carboxylic acid were added 2.7 grams (27.05 mmol) of N-methyl piperazine and 70 ml of pyridine and the mixture was heated to reflux for sixty-eight hours. Pyridine was evaporated therefrom under reduced pressure, ether was added to the residue and washed, purified by silica gel chromatography, and recrystallized from dimethyl formamide to give 175 mg of the title compound. Yield was 15 percent and melting point was 286° C. (with decomposition). Elementary analysis calculated as C₂₀H₂₀FN₃O₅S: C 55.42, H 4.65, N 9.69; Found: C 55.16, H 4.85, N 9.42.

Infrared absorption spectra (KBr, cm⁻¹): 1690, 1630, 1584, 1482, 1456.

Nuclear magnetic resonance spectra δ(CF₃CO₂D): 3.20 (3H, singlet, NCH₃), 3.02 to 4.50

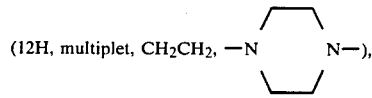

(12H, multiplet, CH₂CH₂, —N   N—), 7.84 (1H, singlet, C₂—H), 8.50 (1H, doublet, C₆—H), 8.86 (1H, doublet, C₉—H).

EXAMPLE 36

Ethyl 8-chloro-1-chloromethyl-7-fluoro-5-oxo-5H-thiazolo(3,2-a)-quinoline-4-carboxylate A mixture of 10.0 grams (33 mmol) of ethyl 7-chloro-6-fluoro-4-hydroxy-2-mercaptoquinoline-3-carboxylate and 5.04 grams (40 mmol) of dichloroacetone was heated with stirring for fifteen hours at 100° C. in 100 ml of ethanol. After cooled, crystals separated out therefrom were collected by filtration to give 11.40 grams of colorless crystals. These crystals were dissolved in 50 grams of sulfuric acid with cooling, stirred for two hours, poured over ice water, crystals separated out were collected by filtration, washed with water, dried with air and recrystallized from dimethyl formamide to give 9.01 grams of the title compound. The yield was 73.2 percent and melting point was 256° C. (with decomposition). Elementary analysis calculated as C₁₅H₁₀FCl₂NO₃S: C 48.18, H 2.69, N 3.74; Found: C 48.16, H 2.70, N 3.58.

Infrared absorption spectra (KBr, cm⁻¹): 3075, 1657, 1610, 1510, 1460, 1040.

Nuclear magnetic resonance spectra δ(CF₃CO₂D): 1.66 (3H triplet, 4.83 (2H, quartet, —OCH₂CH₃), 5.31 (2H, singlet, —CH₂Cl), 8.14 (1H, singlet, C₂—H), 8.45 (1H, triplet, C₆—H), 9.02 (1H, doublet, C₉—H).

EXAMPLE 37

Ethyl 8-chloro-7-fluoro-1-(4-methyl-1-piperazinyl-methyl)-5-oxo-5H-thiazolo(3,2-a)-quinoline-4-carboxylate Two grams (5.3 mmol) of ethyl 8-chloro-1-chloromethyl-7-fluoro-5-oxo-5H-thiazolo(3,2-a)-quinoline-4-carboxylate was dissolved in 20 ml of dimethyl formamide, then 0.88 gram (6.4 mmol) of potassium carbonate and 0.64 gram (6.4 mmol) of N-methyl piperazine were added thereto, and the mixture was heated with stirring for one hour at 80° C. The content was concentrated under reduced pressure, water was added to the residue, crystals separated out therefrom were collected by filtration, washed with water, dried with air and recrystallized from dimethyl formamide to give the title compound in 1.72 grams (74.8 percent) yield. Melting point was 265° to 7° C. (with decomposition). Elementary analysis calculated as C₂₀H₂₁FClN₃O₃S: C 54.85, H 4.83, N 9.60; Found C 54.65, H 4.88, N 9.39.

Infrared absorption spectra (KBr, cm⁻¹): 2800, 1660, 1635, 1602, 1500, 1460.

Nuclear magnetic resonance spectra δ(CF₃CO₂D): 1.68 (3H, triplet, —OCH₂CH₃), 3.12 (3H, singlet, =NCH₃), 2.80 to 4.20

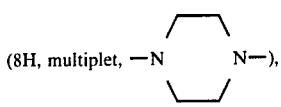

(8H, multiplet, —N͡͡N—), 4.65 (2H, singlet, —CH₂N═), 4.82 (2H, quartet, —OCH₂CH₃), 8.21 (1H, singlet, C₂—H), 8.40 (1H, doublet, C₆—H), 9.38 (1H, doublet, C₉—H).

EXAMPLE 38

8-chloro-7-fluoro-1-(4-methyl-1-piperazinyl)methyl-5-oxo-5H-thiazolo(3,2-a)-quinoline-4-carboxylic acid Ethyl 8-chloro-7-fluoro-1-(4-methyl-1-piperazinyl)-methyl-5-oxo-5H-thiazolo(3,2-a)-quinoline-4-carboxylate (0.72 gram, 1.6 mmol) was heated to reflux for one hour in a mixture of 0.18 gram (3.2 mmol) of potassium hydroxide, 1 ml of ethanol and 5 ml of water. The mixture was then acidified with acetic acid, crystals separated out thereby were collected by filtration, and recrystallized from dimethyl formamide to give 0.45 gram (68.2 percent) of the title compound. Melting point was 303° C. (with decomposition). Elementary analysis calculated as $C_{18}H_{17}FClN_3O_3S \cdot 3H_2O$: C 46.60, H 5.00, N 9.06; Found: C 46.57, H 4.61, N 9.93.

Infrared absorption spectra (KBr, cm⁻¹): 1700, 1590, 1515, 1480.

Nuclear magnetic resonance spectra δ(CF₃CO₂D): 3.10 (3H, singlet, ═NCH₃), 3.50 to 4.30

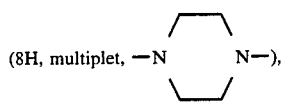

(8H, multiplet, —N͡͡N—), 5.15 (2H, singlet, —CH₂N═), 8.40 (1H, doublet, C₉—H), 8.47 (1H, singlet, C₂—H), 8.95 (1H, doublet, C₆—H).

EXAMPLE 39

Ethyl 8-chloro-1-(N,N-dimethylaminomethyl)-7-fluoro-5-oxo-5H-thiazolo(3,2-a)-quinoline-4-carboxylate A mixture of 1.38 grams (3.7 mmol) of ethyl 8-chloro-1-chloro-methyl-7-fluoro-5-oxo-5H-thiazolo(3,2-a)-quinoline-4-carboxylate, 710 mg (8.7 mmol) of dimethyl amine hydrochloride, and 1.84 grams (17.4 mmol) of sodium carbonate was suspended in 100 ml of ethanol and the whole was heated to reflux. After twenty hours, the reaction mixture was cooled to room temperature and concentrated under reduced pressure. Water was added to the residue. Insoluble matter obtained thereby was collected by filtration, washed with ethanol and recrystallized from dimethyl formamide to give 1.35 grams (66.8 percent yield) of the title compound. Melting point was 276° C.

Infrared absorption spectra (KBr, cm⁻¹): 1655, 1625, 1605, 1500, 1460.

Nuclear magnetic resonance spectra δ(CF₃CO₂D): 1.70 (3H, triplet, —OCH₂CH₃), 3.29 (6H, singlet, —N(CH₃)₂), 4.88 (2H, quartet, —OCH₂CH₃), 5.52 (2H, singlet, —CH₂N═), 8.30 to 8.70 (3H, multiplet, C₂—H, C₆—H, C₉—H).

EXAMPLE 40

8-chloro-1-(N,N-dimethylaminomethyl)-7-fluoro-5-oxo-5H-thiazolo(3,2-a)-quinoline-4-carboxylic acid Ethyl 8-chloro-1-(N,N-dimethylaminomethyl)-7-fluoro-5-oxo-5H-thiazolo(3,2-a)-quinoline-4-carboxylate (1.35 grams, 3.52 mmol) was suspended in 100 ml of 50% aqueous ethanol and, after addition of 10 ml of 2N aqueous solution of sodium hydroxide, the mixture was heated to reflux. After one hour, the reaction solution was cooled to room temperature and ethanol was evaporated therefrom under reduced pressure. To the concentrated residual solution was added acetic acid with cooling to adjust to pH 7.0 and the mixture was stirred for awhile. Crystals separated therefrom were collected by filtration, washed with water, and dried to give 1.08 grams (yield: 86.4 percent) of the title compound. Melting point was 271.5° to 2° C. (with decomposition).

Infrared absorption spectra ($\gamma_{max}^{KBr}$ cm⁻¹): 1690, 1645, 1610, 1500, 1475.

Nuclear magnetic resonance spectra (CF₃CO₂D, δ): 3.30 (6H, singlet, —N(CH₃)₂), 5.52 (2H, wide singlet, —CH₂N═), 8.25 to 8.70 (3H, multiplet, C₂—H, C₆—H, C₉—H).

Elementary analysis calculated as $C_{15}H_{12}ClFN_2O_3S \cdot 1\tfrac{1}{2}H_2O$): C 47.19, H 3.96, N 7.34; C 47.34, H 3.46, N 7.01.

EXAMPLE 41

1-dimethylaminomethyl-7-fluoro-5-oxo-8-(1-piperazinyl)-5H-thiazolo(3,2-a)-quinoline-5-carboxylic acid A mixture of 900 mg (2.54 mmol) of 8-chloro-1-dimethylaminomethyl-7-fluoro-5-oxo-5H-thiazolo(3,2-a)-quinoline-5-carboxylic acid and 2.2 grams (25.4 mmol) of anhydrous piperazine was suspended in 20 ml of pyridine and heated to reflux. After seventeen hours, the reaction solution was cooled to room temperature, pyridine was evaporated therefrom under reduced pressure, ethanol was added to the resulting residue, the insoluble matter obtained was collected by filtration, washed with ethanol and ether, and dried. The resulting crystals were purified by silica gel column chromatography to give the title compound. Yield was 75 mg (7.3 percent) and melting point was 246° C. (with decomposition).

Infrared absorption spectra ($\gamma_{max}^{KBr}$ cm⁻¹): 1680, 1630, 1495, 800.

Nuclear magnetic resonance spectra (CF₃CO₂D) δ: 3.11 (6H, singlet, NCH₃×2), 3.40 to 4.40

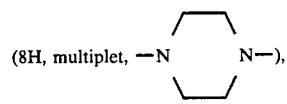

(8H, multiplet, —N͡͡N—), 5.45 (2H, wide singlet, CH₂N═), 7.55 (1H, doublet, C₉—H), 8.32 1H, doublet, C₅—H), 8.46 (1H, singlet, C₁—H).

Elementary analysis calculated as $C_{19}F_{21}FN_4O_3S$: C 56.42, H 5.23, N 13.87; Found: C 56.53, H 5.28, N 13.80.

EXAMPLE 42

(1-(N,N-dimethylaminomethyl)-7-fluoro-8-(4-methyl-1-piperazinyl)-5-oxo-5H-thiazolo(3,2-a)-quinoline-4-carboxylic acid A mixture of 920 mg (2.6 mmol) of 8-chloro-1-(N,N-dimethylamino)-7-fluoro-5-oxo-5H-thiazolo(3,2-a)-quinoline-4-carboxylic acid and 2.6 grams (26 mmol) of N-methyl piperazine was added to 20 ml of pyridine and the whole was heated to reflux. After sixty-five hours, the reaction solution was cooled to room temperature and pyridine was evaporated therefrom under reduced pressure. To the residue was added ethanol, insoluble matter obtained thereby was collected by filtration, and washed with ether. The resulting crystals were purified by subjecting to silica gel column chromatography to give 250 mg (yield: 23 percent) of the title compound. Melting point was 241° to 2° C. (with decomposition).

Infrared absorption spectra (KBr, cm$^{-1}$): 1690, 1630, 1580, 1490.

Nuclear magnetic resonance spectra $\delta(CF_3CO_2D)$: 3.24 (9H, wide singlet, —N(CH$_2$)$_2$, =NCH$_3$), 3.00 to 4.50

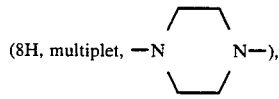

(8H, multiplet, —N⟨⟩N—), 5.51 (2H, wide singlet, —CH$_2$N=), 8.20 to 8.70 (3H, multiplet, C$_2$—H, C$_6$—H, C$_9$—H).

Elementary analysis calculated as C$_{20}$H$_{23}$FN$_4$O$_3$S.½H$_2$O: C 56.26, H 5.66, N 13.11; Found: C 56.32, H 5.41, N 12.87.

EXAMPLE 43

Methyl 8-chloro-7-fluoro-1-methoxymethyl-5-oxo-5H-thiazolo(3,2-a)-quinoline-4-carboxylate Ethyl 8-chloro-1-chloromethyl-7-fluoro-5-oxo-5H-thiazolo(3,2-a)quinoline-4-carboxylate (1.5 grams, 4.0 mmol) was suspended in anhydrous methanol, then sodium methoxide solution prepared from 2.1 grams of metal sodium and 50 ml of anhydrous methanol was added, and the mixture was heated to reflux for twenty minutes. After cooled, water was added to the reaction solution, crystals separated out therefrom were collected by filtration, washed with water, and dried to give 630 mg of the title compound. The yield was 44.4 percent and melting point was 239° to 40° C. Elementary analysis calculated as C$_{15}$H$_{11}$ClFNO$_4$S: C 50.64, H 3.12, N 3.94; Found: C 50.51, H 3.08, N 3.80.

Infrared absorption spectra (KBr, cm$^{-1}$): 1665, 1630, 1610, 1470.

Nuclear magnetic resonance spectra $\delta(CF_3CO_2D)$: 3.79 (3H, singlet, —OCH$_3$), 4.32 (3H, singlet, C(:O)OCH$_3$) 5.11 (2H, singlet, —CH$_2$—), 8.15 (1H, singlet, C$_2$—H), 8.44 (1H, doublet, C$_6$—H), 9.12 (1H, doublet, C$_9$—H).

EXAMPLE 44

8-chloro-7-fluoro-1-methoxymethyl-5-oxo-5H-thiazolo(3,2-a)-quinoline-4-carboxylic acid Methyl 8-chloro-7-fluoro-1-methoxymethyl-5-oxo-5H-thiazolo(3,2-a)quinoline-4-carboxylate (1.8 grams, 3.0 mmol) was suspended in 100 ml of 50% aqueous alcohol, 10 ml of 2N aqueous sodium hydroxide solution was added thereto, and the mixture was heated to reflux for twenty minutes. When the reaction was completed, ethanol was evaporated therefrom under reduced pressure, the residue was adjusted to pH 7.0 with acetic acid, stirred for awhile, crystals separated out thereby were collected by filtration, washed with tetrahydrofuran and ether, and dried with air to give the title compound. The yield was 945 mg (92.1 percent) and melting point was 298° C. (with decomposition). Elementary analysis calculated as C$_{14}$H$_9$ClFNO$_4$S: C 59.20, H 2.65, N 4.10; Found: C 49.11, H 2.60, N 4.00.

Infrared absorption spectra (KBr, cm$^{-1}$): 1690, 1590, 1480.

Nuclear magnetic resonance spectra $\delta(CF_3CO_2D)$: 3.80 (3H, singlet, OCH$_3$), 5.12 (2H, singlet, —CH$_2$O—), 8.15 (1H, singlet, C$_2$—H), 8.25 to 8.70 (1H, multiplet, C$_6$—H), 8.75 to 9.30 (1H, multiplet, C$_9$—H).

EXAMPLE 45

7-fluoro-1-methoxymethyl-8-(4-methyl-1-piperazinyl)-5-oxo-5H-thiazolo(3,2-a)-quinoline-4-carboxylic acid A mixture of 878 mg (2.66 mmol) of 8-chloro-7-fluoro-1-methoxy-methyl-5-oxo-5H-thiazolo(3,2-a)-quinoline-4-carboxylic acid and 2.7 grams (26.6 mmol) of N-methyl piperazine was suspended in 20 ml of pyridine and the suspension was heated to reflux. After fifty-five hours, the reaction solution was evaporated under reduced pressure, ethanol was added to the resulting residue, and insoluble matter obtained thereby was collected by filtration. This was subjected to silica gel column chromatography and recrystallized from aqueous dimethyl formamide to give 220 mg of the title compound. The yield was 20.4 percent and melting point was 243° to 244° C. (with decomposition).

Infrared absorption spectra (KBr, cm$^{-1}$): 1690, 1630, 1580, 1490.

Nuclear magnetic resonance spectra (CF$_3$CO$_2$D, $\delta$): 3.21 (3H, singlet, N—CH$_3$), 3.69 (3H, singlet, —OCH$_3$), 3.35 to 4.50 (8H, multiplet, hydrogen atom in piperazine), 5.12 (2H, singlet, —CH$_2$OCH$_3$), 8.05 (1H, singlet, C$_2$—H), 8.25 (1H, doublet, C$_9$—H), 8.80 (1H, singlet, C$_6$—H).

Elementary analysis calculated as C$_{19}$H$_{20}$FN$_3$O$_4$S.H$_2$O: C 53.89, H 5.2, N 9.92; Found: C 54.23, H 4.8, N 9.69.

EXAMPLE 46

8-chloro-7-fluoro-1-hydroxymethyl-5-oxo-5H-thiazolo(3,2-a)-quinoline-4-carboxylic acid Three grams (0.8 mmol) of ethyl 8-chloro-1-chloromethyl-7-fluoro-5-oxo-5H-thiazolo(3,2-a)quinoline-4-carboxylate was dissolved in 20 ml of dimethyl formamide, 0.72 gram (0.88 mmol) of sodium acetate was added thereto, and the mixture was heated with stirring at 150° C. for twelve hours. The content was concentrated under reduced pressure, water was added thereto, and the resulting crystals which were insoluble in water were collected by filtration. The crystals were suspended in a mixture of 1.28 grams of sodium hydroxide, 80 ml of water and 20 ml of ethanol and the suspension was heated with stirring at 140° C. for two hours. This was then acidified with acetic acid, crystals separated out therefrom were collected by filtration, washed with water, and dried with air and recrystallized from dimethyl formamide to give the title compound. Colorless crystals. The yield was 1.47 grams (56.1 percent). Melting point was 298° to 9° C. (with decomposition). Elementary analysis calculated as $C_{13}H_7ClFNO_4S$: C 47.65, H 2.15, N 4.27; Found: C 47.83, H. 209, N 4.00.

Infrared absorption spectra (KBr, $cm^{-1}$): 1665, 1580, 1480.

Nuclear magnetic resonance spectra $\delta(CF_3CO_2D)$: 5.50 (2H, singlet, —$CH_2OAc$), 8.15 (1H, singlet, $C_2$—H), 8.42 (1H, doublet, $C_6$—H), 9.15 (1H, doublet, $C_9$—H).

EXAMPLE 47

7-fluoro-1-hydroxymethyl-8-(4-methyl-1-piperazinyl)-5-oxo-5H-thiazolo(3,2-a)-quinoline-4-carboxylic acid A mixture of 1.49 grams (4.55 mmol) of 8-chloro-7-fluoro-1-hydroxy-methyl-5-oxo-5H-thiazolo(3,2-a)quinoline 4-carboxylic acid, 4.6 grams (45.5 mmol) of N-methyl piperazine and 50 ml of pyridine was heated to reflux at 150° C. for seventy-two hours. After cooled, crystals separated out therefrom were collected by filtration and recrystallized from dimethyl formamide to give the title compound. Colorless crystals. The yield was 700 mg (39.3 percent) and melting point was 302° to 3° C. (with decomposition). Elementary analysis calculated as $C_{18}H_{18}FN_3O_4$: C 55.23, H 4.64, N 10.74; Found: C 55.15, H 4.52, N 10.30.

Infrared absorption spectra (KBr, $cm^{-1}$): 1670, 1625, 1580, 1490, 1380, 1275.

Nuclear magnetic resonance spectra $\delta(CF_3CO_2D)$: 3.15 (3H, singlet, =$NCH_3$), 3.00 to 4.50 (8H, multiplet, —N N—), 5.31 (2H singlet, —$CH_2OH$), 7.97 (1H, singlet, $C_2$—H), 8.25 (1H, doublet, $C_6$—H), 8.69 (1H, doublet, $C_9$—H).

EXAMPLE 48

1-Acetoxymethyl-7-fluoro-8-(4-methyl-1-piperazinyl)-5-oxo-5H-thiazolo(3,2-a)-quinoline-4-carboxylic acid 7-fluoro-1-hydroxymethyl-8-(4-methyl-1-piperazinyl)-5-oxo-5H-thiazolo(3-2-a)-quinoline-4-carboxylic acid (270 mg, 0.69 mmol) was dissolved in 30 ml of pyridine, then 300 mg (2.9 mmol) of acetic anhydride was added thereto, and the mixture was heated with stirring at 90° C. for three hours. Insoluble matter obtained thereby was filtered off, the mother liquor was concentrated, and the crystalline residue was recrystallized from a mixture of chloroform and ether to give the title compound. Colorless crystals. The yield was 220 mg (73.6 percent) and melting point was 237° to 8° C. (with decomposition).

Elementary analysis calculated as $C_{20}H_{20}FN_3O_5S\cdot H_2O$: C 53.21, H 4.91, N 9.31; Found: C 53.50, H 4.54, N 8.86.

Infrared absorption spectra (KBr, $cm^{-1}$): 1750, 1690, 1630, 1485, 1180, 1270, 1208.

Nuclear magnetic resonance spectra $\delta(CF_3CO_2D)$: 2.35 (3H, singlet, $COCH_3$), 3.19 (3H, singlet, =$NCH_3$), 3.30 to 4.50

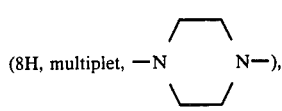

(8H, multiplet, —N N—), 5.89 (2H, singlet, —$CH_2OA_c$), 7.90 to 8.50 (3H, multiplet, $C_2$—H, $C_6$—H, $C_9$—H).

EXAMPLE 49

8-chloro-7-fluoro-5-oxo-1-phenyl-5H-thiazolo(3,2-a)quinoline-4-carboxylic acid

Two grams (6.6 mmol) of ethyl 7-chloro-6-fluoro-4-hydroxy-2-mercaptoquinoline-3-carboxylate was suspended in 10 ml of ethanol, then 1.3 grams (6.5 mmol) of phenacyl bromide was added thereto, and the mixture was heated to reflux with vigorous stirring for three hours. After cooled, crystals separated out therefrom were collected by filtration, dried with air, and 2.08 grams of colorless powder was obtained. To this was added 4.5 grams of concentrated sulfuric acid, the mixture was heated at 80° to 90° C. for ten minutes, cooled, poured into ice water, crystals separated out were collected by filtration, washed with water, and dried with air. This was suspended in a mixture of 0.29 gram (7.2 mmol) of sodium hydroxide, 60 ml of water and 10 ml of ethanol and the whole mixture was heated to reflux for two hours and a half. This was then acidified with acetic acid, crystals separated out were collected by filtration, washed with water, dried with air, and recrystallized from dimethyl formamide to give the title compound as colorless crystals in 1.19 grams (48.2 percent yield). Melting point was 330° C. (with decomposition). Elementary analysis calculated as $C_{18}H_9ClFNO_3S$: C 57.84, H 2.43, N 3.75; Found C 58.22, H 2.11, N 3.67.

Infrared absorption spectra (KBr, $cm^{-1}$): 3080, 1695, 1585, 1460, 1260, 1045, 800.

Nuclear magnetic resonance spectra $\delta(CF_3CO_2D)$: 7.40 to 8.00 (7H, multiplet, $C_2$—H, phenyl group—H), 8.30 (1H, doublet, $C_6$—H).

EXAMPLE 50

7-fluoro-8-(4-methyl-1-piperazinyl)-5-oxo-1-phenyl-5H-thiazolo(3,2-a)-quinoline-4-carboxylic acid and 8-chloro-7-(4-methyl-1-piperazinyl)-5-oxo-1-phenyl-5H-thiazolo(3,2-a)-quinoline-4-carboxylic acid A mixture of 970 mg (2.60 mmol) of 8-chloro-7-fluoro-5-oxo-1-phenyl-5H-thiazolo(3,2-a)-quinoline-4-carboxylic acid, 2.6 grams (26 mmol) of N-methyl piperazine and 50 ml of pyridine was heated to reflux for seventy-two hours. The content was concentrated under reduced pressure, water was added to the residue, insoluble matter obtained thereby was collected by filtration, washed with water, dried and recrystallized from dimethyl formamide to give 7-fluoro-8-(4-methyl-1-piperazinyl)-5-oxo-1-phenyl-5H-thiazolo(3,2-a)-quinoline-4-carboxylic acid as colorless crystals in the yield of 494 mg (43.4 percent). Melting point was 300° C. (with decomposition). Elementary analysis calculated as $C_{23}H_{20}FN_3O_3S$: C 63.14, H 4.61, N 9.60; Found: C 63.19, H 4.45, N 10.00.

Infrared absorption spectra (KB5, $cm^{-1}$): 1695, 1625, 1480, 1260, 760.

Nuclear magnetic resonance spectra $\delta(CF_3CO_2D)$: 3.90 (3H, singlet, —$NCH_3$), 3.00 to 4.00

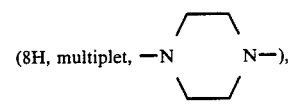

(8H, multiplet, —N N—), 7.30 (1H, doublet, $C_9$—H), 7.65 (5H, singlet, phenyl group), 7.75 (1H, singlet, $C_2$—H), 8.25 (1H, doublet, $C_6$—H).

Crystals obtained from the mother liquor were recrystallized from dimethyl formamide to give 8-chloro-7-(4-methyl-1-piperazinyl)-5-oxo-1-phenyl-5H-thiazolo(3,2-a)quinoline-4-carboxylic acid as colorless crystals in the yield of 120 mg (10.2 percent) with a melting point of 207° to 9° C. (with decomposition). Elementary analysis calculated as $C_{23}H_{20}ClN_3O_3S$: C 60.86, H 4.44, N 9.26; Found: C 60.83, H 4.49, N 9.35.

Infrared absorption spectra (KBr, cm$^{-1}$): 1690, 1575, 1500, 1480, 1140, 800.

Nuclear magnetic resonance spectra $\delta(CF_3CO_2D)$: 3.10 (3H, singlet, $=NCH_3$) 3.00 to 4.0

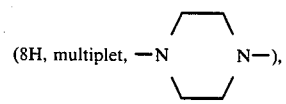

(8H, multiplet, $-N\quad N-$), 7.20 to 7.90 (multiplet, phenyl group—H, $C_2$—H, $C_6$—H, 8.15 (1H, singlet, $C_9$—H).

EXAMPLE 51

Ethyl 8-chloro-7-fluoro-1,2-dimethyl-5-oxo-5H-thiazolo(3,2-a)-quinoline-4-carboxylate (a) To three grams (9.94 mmol) of ethyl 7-chloro-6-fluoro-4-hydroxy-2-mercaptoquinoline-3-carboxylate was added a solution of 0.23 gram of sodium (9.94 mmol) in 100 ml of ethanol and the mixture was stirred at room temperature for eighteen hours after addition of 1.3 grams (12.20 mmol) of 3-chloro-2-butanone. The content was concentrated under reduced pressure, 40 ml of water was added to the residue, crystals obtained thereby were collected by filtration, washed with water and then with ether, dried, and 3.56 grams (96% yield) of ethyl 7-chloro-6-fluoro-4-oxo-2-(2-oxobutyl-3-thio)-1,4-dihydroquinoline-3-carboxylate was obtained. Melting point was 222° to 224° C. (with decomposition). Elementary analysis calculated as $C_{17}H_{16}ClFNO_4S$: C 51.68, H 4.06, N 3.76; Found: C 51.72, H 4.32, N 3.69.

Infrared absorption spectra (KBr, cm$^{-1}$): 3220, 1680, 1600, 1470.

Nuclear magnetic resonance spectra $\delta(CF_3CO_2D)$: 1.65 (3H, triplet, $-OCH_2\underline{CH_3}$), 1.73 (3H, doublet, SCH$\underline{CH_3}$), 1.92 (3H, singlet, $-CO\underline{CH_3}$), 3.96 to 4.50 (1H, multiplet, $=\underline{CH}CH_3$), 4.74 (2H, quartet, $-O\underline{CH_2}CH_3$), 8.24 (1H, doublet, $C_5$—H), 9.30 (1H, doublet, $C_8$—H).

(b) To 3.1 grams (8.34 mmol) of ethyl 7-chloro-6-fluoro-4-oxo-2-(2-oxobutyl-3-thio)-1,4-dihydroquinoline-3-carboxylate was added 15 grams of sulfuric acid and the mixture was heated with stirring at 70° C. for ten minutes. The content was cooled, added to 20 grams of ice, crystals separated out therefrom were collected by filtration, washed with water and then with ether, and dried to give 2.66 grams (90 percent yield) of the title compound, melting point 223° to 227° C. (with decomposition). Elementary analysis calculated as $C_{16}H_{13}ClFNO_3S$: C 54.31, H 3.70, N 3.95; Found: C 54.62, H 3.81, N 4.07.

Infrared absorption spectra (KBr, cm$^{-1}$): 1660, 1610, 1502, 1452.

Nuclear magnetic resonance spectra $\delta$ ($CF_3CO_2D$): 1.74 (3H, triplet, $-OCH_2\underline{CH_3}$), 2.76 (3H, singlet, $C_2$—$CH_3$), 3.20 (3H, singlet, $\overline{C_2}$—$CH_3$), 4.85 (2H, quartet, $-O\underline{CH_2}CH_3$), 8.46 (1H, doublet, $C_6$—H), 9.00 (1H, doublet, $\overline{C_9}$—H.

EXAMPLE 52

8-chloro-7-fluoro-1,2-dimethyl-5-oxo-5H-thiazolo(3,2-a)-quinoline-4-carboxylic acid To 2.66 grams (7.52 mmol) of ethyl 8-chloro-7-fluoro-1,2-dimethyl-5-oxo-5H-thiazolo(3,2-a)-quinoline-4-carboxylate were added 40 ml of ethanol and a solution of 1.5 grams (37.60 mmol) of sodium hydroxide in 120 ml of water and the mixture was heated to reflux for five hours in an oil bath. Ethanol was evaporated therefrom under reduced pressure, acetic acid was added to the residue so that it was made acidic, crystals separated out thereby were collected by filtration, washed with water and then with ethanol, dried and the resulting crystals were recrystallized from dimethyl formamide to give 2.3 grams (94 percent yield) of the title compound, melting point 294° to 296° C. (with decomposition). Elementary analysis calculated as $C_{14}H_{10}ClFNO_3S$: C 51.62, H 2.78, N 4.29; Found: C 51.84, H 2.69, N 4.51.

Infrared absorption spectra (KBr, cm$^{-1}$): 1690, 1590, 1510, 1470, 1440.

Nuclear magnetic resonance spectra $\delta$ ($CF_3CO_2D$): 2.70 (3H, singlet, $C_2$—$CH_3$), 3.14 (3H, singlet, $C_1$—$CH_3$), 8.46 (1H, doublet, $C_6$—H), 8.95 (1H, doublet, $C_9$—H).

EXAMPLE 53

7-fluoro-8-(4-methyl-1-piperazinyl)-1,2-dimethyl-5-oxo-5H-thiazolo(3,2-a)-quinoline-4-carboxylic acid A mixture of 1.0 gram (3.1 mmol) of 8-chloro-7-fluoro-1,2-dimethyl-5-oxo-5H-thiazolo(3,2-a)-quinoline-4-carboxylic acid, 3.1 grams (31.0 mmol) of N-methyl piperazine and 40 ml of pyridine was heated to reflux in an oil bath for forty-eight hours. The content was then concentrated under reduced pressure, water was added to the residue, the insoluble matter thereby obtained were collected by filtration, washed with water and then with ethanol, dried, and the resulting crystals were recrystallized from pyridine for three times to give 0.34 gram (31 percent yield) of the title compound, colorless crystals, melting point 283° to 285° C. (with decomposition). Elementary analysis calculated as $C_{19}H_{20}ClFNO_3S$: C 58.59, H 5.17, N 10.78: Found: C 58.71, H 5.18, N 10.51.

Infrared absorption spectra (KBr, cm$^{-1}$): 1690, 1630, 1580, 1485.

Nuclear magnetic resonance spectra $\delta$ ($CF_3CO_2D$): 2.67 (3H, singlet, $C_2$—$CH_3$), 3.12 (3H, singlet, $C_1$—$CH_3$), 3.22

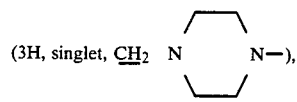

(3H, singlet, $\underline{CH_2}$ N   N—), 3.30 to 4.50

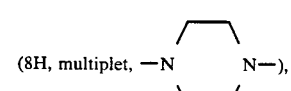

(8H, multiplet, $-N\quad N-$), 8.17 (1H, doublet, $C_9$—H), 8.34 (1H, doublet, $C_6$—H).

EXAMPLE 54

Ethyl 2-chloro-3-fluoro-5-oxo-8,9,10,11-tetrahydro-5H-benzothiazolo(3,2-a)-quinoline-6-carboxylate (a) To three grams (10 mmol) of ethyl 7-chloro-6-fluoro-4-hydroxy-2-mercaptoquinoline 3-carboxylate was added a solution of 0.25 gram of sodium (11 mmol) in 100 ml of ethanol and the mixture was stirred at room temperature for twenty hours after addition of 1.59 grams (12 mmol) of 2-chlorocyclohexanone. Then the mixture was heated to reflux for three hours more. Ethanol was evaporated therefrom under reduced pressure, water was added to the residue and, after being washed with water, it was further washed with ethanol and ether and finally dried to give 3.62 grams (91 percent yield) of ethyl 7-chloro-6-fluoro-4-hydroxy-2-(2-oxocyclohexylthio)-quinoline-3-carboxylate, melting point 252° to 257° C. (with decomposition.) Elementary analysis calculated as $C_{18}H_{17}ClFNO_4S$: C 54.34, H 4.30, N 3.52; Found: C 54.56, H 4.42, N 3.59.

Infrared absorption spectra (KBr, cm$^{-1}$): 3240, 1682, 1600, 1471.

Nuclear magnetic resonance spectra δ (CF$_3$CO$_2$D): 1.59 (3H, triplet, —OCH$_2$CH$_3$), 1.10 to 2.80

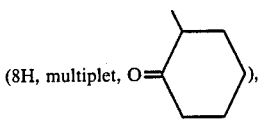

(8H, multiplet, O=⟨⟩), 4.12 to 4.45

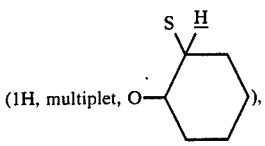

(1H, multiplet, O—⟨⟩), 4.72 (2H, quartet, —OCH$_2$CH$_3$), 8.18 (1H, doublet, C$_5$—H), 9.32 (1H, doublet, C$_8$—H).

(b) To 3.56 grams (8.948 mmol) of ethyl 7-chloro-6-fluoro-4-hydroxy-2-(2-oxocyclohexylthio)-quinoline-3-carboxylate was added 17 grams of sulfuric acid and the mixture was heated with stirring at 70° to 80° C. for twenty minutes. After cooled, it was added to 150 grams of ice, crystals separated out thereby were collected by filtration, washed with water and then with ethanol and ether, and dried to give 3.26 grams (96 percent yield) of the title product, gray crystals, melting point 294° to 297° C. (with decomposition). Elementary analysis calculated as $C_{18}H_{15}ClFNO_3S$: C 56.91, H 3.98, N 3.68; Found: C 57.20, H 4.12, N 3.59.

Infrared absorption spectra (KBr, cm$^{-1}$): 1670, 1630, 1610, 1506.

Nuclear magnetic resonance spectra δ (CF$_3$CO$_2$D): 1.65 (3H, triplet, —OCH$_2$CH$_3$, 1.90 to 2.56 (4H, multiplet, C$_{9,10}$—CH$_2$), 2.80 to 3.29 (2H, multiplet, C$_8$—CH$_2$), 3.30 to 3.82 (2H, multiplet, C$_{11}$—CH$_2$), 4.82 (2H, quartet, —OCH$_2$CH$_3$, 8.41 (1H, doublet, C$_4$—H), 8.86 (1H, doublet, C$_1$—H).

EXAMPLE 55

2-chloro-3-fluoro-5-oxo-8,9,10,11-tetrahydro-5H-benzothiazolo(3,2-a)-quinoline-6-carboxylic acid To three grams (7.89 mmol) of ethyl 2-chloro-3-fluoro-5-oxo-8,9,10,11-tetrahydro-5H-benzothiazolo(3,2-a)-quinoline-6-carboxylate was added a solution of 1.6 grams (40.10 mmol) of sodium hydroxide in 300 ml of water and the mixture was heated to reflux for twenty hours. After cooled, the solution was acidified with acetic acid, stirred for one hour, crystals separated out thereby were collected by filtration, the crystals were washed with water and then with ethanol, and dried to give 2.65 grams (95 percent yield) of pale brown crystals—the title product. Melting point was 311° to 313° C. (with decomposition). Elementary analysis calculated as $C_{16}H_{11}ClFNO_3S$: C 54.62, H 3.15, N 3.98: Found: C 54.75, H 3.42, N 3.89.

Infrared absorption spectra (KBr, cm$^{-1}$), 1695, 1590, 1510, 1455.

Nuclear magnetic resonance spectra δ (CF$_3$CO$_2$D): 1.81 (4H, multiplet, C$_{9,10}$—CH$_2$), 2.76 to 3.29 (2H, multiplet, C$_8$—CH$_2$—), 3.30 to 3.82 (2H, multiplet, C$_{11}$—CH$_2$—), 8.42 (1H, doublet, C$_4$—HO, 8.86 (1H, doublet, C$_1$—H).

EXAMPLE 56

3-fluoro-2-(4-methyl-1-piperazinyl)-5-oxo-8,9,10,11-tetrahydro-5H-benzothiazolo(3,2-a)-quinoline-6-carboxylic acid To one gram (2.84 mmol) of 2-chloro-3-fluoro-5-oxo-8,9,10,11-tetrahydro-5H-benzothiazolo(3,2-a)quinoline 6-carboxylic acid were added 2.8 grams (28.4 mmol) of N-methyl piperazine and 50 ml of pyridine and the mixture was heated to reflux in an oil bath for fifty-four hours. Pyridine was evaporated therefrom under reduced pressure, the residue was washed with ether and then with water, and dried. The resulting crystals were recrystallized from pyridine twice to give 146 mg (12 percent yield) of the title compound in pale yellow crystals melting at 283° to 285° C. (with decomposition). Elementary analysis calculated as $C_{21}H_{22}FN_2O_3S$: C 60.70, H 5.33, N 10.11; Found: C 60.82, H 5.54, N 10.28.

Infrared absorption spectra (KBr, cm$^{-1}$): 1692, 1630, 1580, 1482.

Nuclear magnetic resonance spectra δ (CF$_3$CO$_2$D): 1.62 to 2.48 (4H, multiplet, C$_{9,10}$—CH$_2$), 2.65 to 4.42

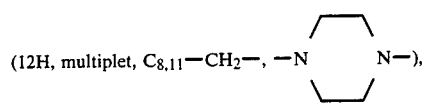

(12H, multiplet, C$_{8,11}$—CH$_2$—, —N⟨⟩N—), 3.19 (3H, singlet, CH$_3$N), 8.14 (1H, doublet, C$_1$—H), 8.31 (1H, doublet, C$_4$—H).

EXAMPLE 57

Ethyl 2-chloro-3-fluoro-7a-methyl-5-oxo-7a,8,9,10-tetrahydro-5H-benzothiazolo(3,2-a)-quinoline-6-carboxylate (a) To three grams (9.94 mmol) of ethyl 7-chloro-6-fluoro-4-hydroxy-2-mercaptoquinoline 3-carboxylate was added a solution of 0.23 gram of sodium (9.94 mmol) in 50 ml of ethanol and the mixture was stirred for about ten minutes. Then 1.7 grams of 2-chloro-2- methyl cyclohexanone (11.43 mmol) was added thereto and the mixture was heated to reflux in an oil bath for twenty-four hours. Ethanol was evaporated therefrom under reduced pressure, water was added to the residue, crystals separated out thereby were collected by filtration, washed with water, and the crystals obtained upon drying were recrystallized from ethanol to give 1.97 grams (48 percent yield) of ethyl 7-chloro-6-fluoro-4-hydroxy-2-(1-methyl-2-oxocyclohexylthio)quinoline 3-carboxylate, yellow crystals, melting at 214° to 217° C. (with decomposition). Elementary analysis calculated as $C_{19}H_{19}ClFNO_4S$: C 55.40, H 4.64, N 3.40; Found: C 55.52, H 4.81, N 3.46.

Infrared absorption spectra (KBr, cm$^{-1}$): 1730, 1680, 1595, 1470.

Nuclear magnetic resonance spectra δ (CDCl$_3$): 1.41 (3H, triplet, —OCH$_2$CH$_3$ 1.53 (3H, singlet, —CH$_3$), 1.20 to 2.80

(8H, multiplet, O=⬡), 4.40 (2H, quartet, —OCH$_2$CH$_3$), 7.35 (1H, doublet, C$_5$—H), 8.71 (1H, doublet, C$_8$—H).

(b) To 1.14 grams (2.77 mmol) of ethyl 7-chloro-6-fluoro-4-hydroxy-2-(1-methyl-2-oxocyclohexylthio)-quinoline-3-carboxylate was added five grams of sulfuric acid and the mixture was heated at 70° C. for five minutes. After cooled, it was added to ten grams of ice, crystals separated out thereby were collected by filtration, washed with water, dried, and the resulting yellow crystals were recrystallized from ethanol to give 0.64 gram (59 percent yield) of the title compound in colorless crystals melting at 196° to 200° C. (with decomposition). Elementary analysis calculated as $C_{19}H_{17}ClFNO_3S$: C 57.94, H 4.35, N 3.55; Found: C 58.10, H 4.38, N 3.72.

Infrared absorption spectra (KBr, cm$^{-1}$): 1750, 1645, 1615, 1470.

Nuclear magnetic resonance spectra δ (CDCl$_3$): 1.45 (3H, triplet, —OCH$_2$CH$_3$, 1.64 (3H, singlet, C$_{7a}$—CH$_3$), 1.80 to 2.90

(6H, multiplet, ⬡), 4.42 (2H, quartet, —OCH$_2$CH$_3$), 6.07 (1H, triplet, C$_{11}$—H), 7.80 (1H, doublet, C$_1$—H), 8.07 (1H, doublet, C$_4$—H).

EXAMPLE 58

2-chloro-3-fluoro-7a-methyl-5-oxo-6a,8,9,10-tetrahydro-5H-benzothiazolo(3,2-a)-quinoline-6-carboxylic acid To 470 mg (1.19 mmol) of ethyl 2-chloro-3-fluoro-7a-methyl-5-oxo-7a,8,9,10-tetrahydro-5H-benzothiazolo(3,2-a)quinoline 6-carboxylate were added 15 ml of ethanol and a solution of 330 mg (5.97 mmol) of potassium hydroxide in 1 ml of water and the mixture was heated to reflux for one hour. Ethanol was evaporated therefrom under reduced pressure, 5 ml of water was added to the residue, the mixture was acidified with acetic acid with cooling, crystals separated out therefrom were collected by filtration, washed with water, and dried to give 340 mg (90 percent yield) of the title compound in colorless crystals melting at 251° to 254° C. (with decomposition). Elementary analysis calculated as $C_{17}H_{13}ClFNO_3S$: C 55.81, H 3.58, N 3.82; Found: C 55.95, H 3.60, N 3.95.

Infrared absorption spectra (KBr, cm$^{-1}$): 1706, 1590, 1490, 1452.

Nuclear magnetic resonance spectra δ(CF$_3$CO$_2$D): 1.76 (3H, singlet, C$_{7a}$—CH$_3$), 1.90 to 2.80 (tH, multiplet, C$_{8,9,10}$—H), 6.50 to 6.65 (1H, multiplet, C$_{11}$—H), 8.12 (1H, Singlet, C$_1$—H), 8.34 (1H, singlet, C$_4$—H).

EXAMPLE 59

3-fluoro-7a-methyl-2-(4-methyl-1-piperazinyl)-5-oxo-7a,8,9,10-tetrahydro-5H-benzothiazolo(3,2-a)-quinoline-6-carboxylic acid To 390 mg (1.07 mmol) of 2-chloro-2-fluoro-7a-methyl-5-oxo-7a,8,9,10-tetrahydro-5H-benzothiazolo(3,2,-a)-quinoline-6-carboxylic acid were added 1.10 grams (10.70 mmol) of N-methyl piperazine and 60 ml of pyridine and the mixture was heated to reflux in an oil bath for sixty-eight hours. Pyridine was evaporated therefrom under reduced pressure and to the residue was added ether, the resulting crystals were collected by filtration, washed with water and then with ether, dried, and the resulting gray crystals were recrystallized from dimethyl formamide to give 140 mg (30 percent yield) of the title compound melting at 249° to 251° C. (with decomposition). Elementary analysis calculated as $C_{22}H_{24}FN_3O_3S$: C 61.52, H 5.63, N 9.78; Found: C 61.64, H 5.8, N 9.62.

Infrared absorption spectra (KBr, cm$^{-1}$): 1715, 1629, 1585, 1490.

Nuclear magnetic resonance spectra δ (CF$_3$CO$_2$D): 1.82 (3H, singlet, C$_{7a}$—CH$_3$), 1.80 to 2.85 (6H, multiplet, C$_{8,9,10}$—H), 3.21 (3H, singlet, NCH$_3$), 3.00 to 4.50

(8H, multiplet, —N⬡N—), 6.50 to 6.65 (1H, multiplet, C$_{11}$—H), 7.60 (1H, doublet, C$_1$—H), 8.15 (1H, doublet, C$_4$—H).

EXAMPLE 60

Ethyl 7-chloro-6-fluoro-4-oxo-4H-(1,3)thiazeto(3,2-a)-quinoline-3-carboxylate

A mixture of 2.0 grams (6.63 mmol) of ethyl 7-chloro-6-fluoro-4-hydroxy-a-mercaptoquinoline-3-carboxylate and 1.96 grams (7.3 mmol) of diiodomethane was stirred at room temperature for one hour in 30 ml of dimethyl formamide in the presence of 2.02 grams (14.6 mmol) of potassium carbonate. Dimethyl formamide was evaporated therefrom under reduced pressure, water and ether were added to the residue, crystals separated out therefrom were collected by filtration, washed with water, dried and recrystallized from dimethyl formamide to give 910 mg (43.8 percent yield) of ethyl 7-chloro-6-fluoro-4-oxo-4H-(1,3)-thiazeto(3,2-a)-quinoline-3-carboxylate melting at 302° to 304° C. (with decomposition). Elementary analysis calculated as $C_{13}H_9ClFNO_3S$: C 49.77, H. 2.89, N 4.46; Found: C 49.61, H 2.92, N 4.63.

Infrared absorption spectra (KBr, cm$^{-1}$): 1710, 1595, 1370, 795.

Nuclear magnetic resonance spectra δ (CF$_3$CO$_2$D): 1.47 (3H, triplet, OCH$_2$CH$_3$), 4.53 (2H, quartet, OCH$_2$CH$_3$), 6.14 (2H, singlet, —N—CH$_2$S—), 7.92 (1H, doublet, C$_6$—H), 8.14 (1H, doublet, C$_8$—H).

EXAMPLE 61

7-chloro-6-fluoro-4-oxo-(1,3)thiazeto(3,2-a)quinoline-3-carboxylic acid

Ethyl 7-chloro-6-fluoro-4-oxo-4H-(1,3)thiazeto(2,1-a)-quinoline-3-carboxylate (365 mg. 1.16 mmol) was dissolved in 3.5 ml of concentrated sulfuric acid and the solution was heated at 80° C. for seven hours. This was poured into ice flakes, crystals separated out thereby were collected by filtration, washed with water, dried and recrystallized from dimethyl formamide to give 258 mg of the title compound. The yield was 77.6 percent and the melting point was 284° to 287° C. (with decomposition). Elementary analysis calculated as $C_{11}H_5ClFNO_3S$: C 46.25, H 1.76, N 4.90; Found: C 46.14, H 1.73, N 4.73.

Infrared absorption spectra (KBr, cm$^{-1}$): 1700, 1600, 805.

Nuclear magnetic resonance spectra δ (CF$_3$CO$_2$D): 6.15 (2H, singlet, —NCH$_2$S—), 7.85 (1H, doublet, C$_5$—H), 8.24 (1H, doublet, C$_8$—H).

EXAMPLE 62

Ethyl 1-methyl-7,8 methylenedioxy-5-oxo-1,2-dihydro-5H-thiazolo(3,2-a)-quinoline-carboxylate A mixture of one gram of ethyl 4-hydroxy-2-mercapto-6,7-methylene-dioxyquinoline-3-carboxylate and 1.38 grams of potassium carbonate was added to 50 ml of dimethyl formamide and, with stirring at room temperature, 1.03 grams of 1,2-dibromopropane was dropped therein. The mixture was then stirred at 60° C. for seven hours. When the reaction was completed, the solvent was evaporated therefrom under reduced pressure, crystals thereby separated out were well washed with water and recrystallized from 30 ml of ethanol to give 930 mg of the title compound in colorless crystals melting at 197° to 205° C. Elementary analysis calculated as $C_{16}H_{15}O_5NS$: C 57.65, H 4.54, N 4.21, S 9.62; Found: C 57.85, H 4.69, N 4.31, S 9.82.

Infrared absorption spectra (KBr, cm$^{-1}$): 1710, 1670, 1630.

Nuclear magnetic resonance spectra δ (CDCl$_3$): 1.45 (3H, doublet, C$_1$—CH$_3$), 1.41 (3H, triplet, —OCH$_2$—CH$_3$), 2.89 (1H, doublet, C$_2$—H), 3.60 (1H, double doublet, C$_2$—H), 4.36 (2H, quartet, —OCH$_2$CH$_3$), 4.8 to 5.2 (1H, wide singlet, C$_1$—H), 6.0 (2H, singlet, —OCH$_2$O—), 6.62 (1H, singlet, C$_9$—H), 7.65 (1H, singlet, C$_6$—H).

EXAMPLE 63

1-methyl-7,8-methylenedioxy-5-oxo-1,2-dihydro-5H-thiazolo(3,2-a)-quinoline-4-carboxylic acid Ethyl 1-methyl-7,8-methylenedioxy-5-oxo-1,2-dihydro-5H-thiazolo(3,2-a)-quinoline-4-carboxylate (930 mg) was dissolved in a solution of one gram of sodium hydroxide in a mixture of 20 ml of water and 20 ml of ethanol. The solution was stirred at 60° C. for thirty minutes. After the reaction was completed, ethanol was evaporated therefrom under reduced pressure and neutralized with acetic acid with ice cooling to give crystals. The crystals separated out therefrom were collected by filtration, well washed with water, and recrystallized from 100 ml of dimethyl formamide to give 610 mg of the title compound melting at higher than 302° C. Elementary analysis calculated as $C_{14}H_{11}NO_5S$: C 55.08, H 3.63, N 4.59; Found: C 55.19, H 3.57, N 4.48.

Infrared absorption spectra (KBr, cm$^{-1}$): 3450, 1690, 1630.

Nuclear magnetic resonance spectra δ (CF$_3$CO$_2$D): 1.75 (3H, doublet, —CH$_3$), 3.40 (2H, doublet, C$_2$—H), 4.0 (1H, triplet, C$_1$—H), 6.30 (2H, singlet, —OCH$_2$O—), 7.25 (1H, singlet, C$_9$—H), 7.75 (1H, singlet, C$_6$—H).

EXAMPLE 64

Ethyl 7.8-methylenedioxy-5-oxo-1-tetrahydropyranyl-oxymethyl-1,2-dihydro-5H-thiazolo(3,2-a)-quinoline-3-carboxylate A mixture of one gram of ethyl 4-hydroxy-2-mercapto-6,7-methylene-dioxyquinoline 3-carboxylate and 1.4 grams of potassium carbonate was added to 50 ml of dimethyl formamide. 1,2-Dibromo-3-tetrahydropyranyloxypropane (1.23 grams) was dropped into the solution with stirring at room temperature. After the dropping was completed, the mixture was heated at 80° C. for three hours with stirring, allowed to stand at room temperature overnight, then the solvent was evaporated therefrom under reduced pressure, the residue was extracted with 100 ml of chloroform, and the extract was washed with water for three times. Chloroform was evaporated therefrom under reduced pressure whereupon the residue was crystallized. The crystals were collected by filtration and recrystallized from fifty ml of ethanol to give one gram of the title compound melting at 152° to 7° C. Elementary analysis calculated as $C_{21}H_{23}NO_7S$: C 58.19, H 5.35, N 3.23, Found: C 58.35, H 5.51, N 3.18.

Infrared absorption spectra (KBr, cm$^{-1}$): 1660, 1610, 1500, 1480, 1200, 1138.

Nuclear magnetic resonance spectra δ (CDCl$_3$): 1.45 (3H, triplet, —OCH$_2$CH$_3$), 1.65 (6H, wide singlet, C$_3$', C$_4$', C$_5$'—H of tetrahydropyranyl group), 3.30 to 4.0 (6H, multiplet, C$_6$'—H of tetrahydropyranyl group, C$_1$—CH$_2$—O—, C$_2$—H), 4.40 (2H, quartet, —OCH$_2$CH$_3$), 4.90 to 5.40 (2H, wide singlet, C$_1$—H, C$_2$'—H of tetrahydropyranyl group), 6.01 (2H, singlet, —OCH$_2$O—), 6.79 (1H, singlet, C$_9$—H), 7.67 (1H, singlet, C$_6$—H).

EXAMPLE 65

1-Hydroxymethyl-7,8-methylenedioxy-5-oxo-1,2-dihydro-5H-thiazolo(3,2-a)-quinoline-4-carboxylic acid One gram of ethyl 7,8-methylenedioxy-5-oxo-1-tetrahydropyranyl-oxymethyl-1,2-dihydro-5H-thiazolo(3,2-a)-quinoline-4-carboxylate was dissolved in a solution of 184 mg of sodium hydroxide in a one-to-one ratio mixture (50 ml) of water and ethanol and the whole mixture was stirred at 80° C. for two hours. When the reaction was completed, ethanol was evaporated therefrom under reduced pressure, then neutralized with acetic acid with ice cooling, crystals separated out thereby were collected by filtration, and dried with air. The resulting crystals were dissolved in ten ml of trifluoroacetic acid and the solution was stirred at room temperature for one hour. After the reaction was completed, the reaction solution was poured over 50 ml of ice water, crystals separated out were collected by filtration, well washed with water, and then washed with ethanol. This was finally dried under reduced pressure to give 620 mg of the title compound which melted at higher than 320° C. Elementary analysis calculated as $C_{14}H_{11}NO_6S.H_2O$: C 49.48, H 3.29, N 4.15; Found: C 50.36, H 3.38, N 3.87.

Infrared absorption spectra (KBr, cm$^{-1}$): 3300, 1680, 1630, 1270.

Nuclear magnetic resonance spectra $\delta$ ($CF_3CO_2D$): 4.20 (4H, doublet, —$\underline{CH_2}OH$, $C_2$—H), 5.7 to 6.2 (1H, broad, $C_1$—H), 6.30 (2H, singlet, —$OCH_2O$—), 7.41 (1H, singlet, $C_9$—H), 7.75 (1H, singlet, $C_6$—H).

EXAMPLE 66

Ethyl 1-methyl-7,8-methylenedioxy-5-oxo-5H-thiazolo(3,2-a)-quinoline-4-carboxylate Five hundred milligrams of ethyl 4-hydroxy-2-mercapto-6,7-methyl-enedioxyquinoline-3-carboxylate was dissolved in thirty milliliters of ethanol, then 180 mg of chloroacetone was added thereto, and the mixture was heated to reflux with stirring for four hours. After the reaction was completed, ethanol was evaporated therefrom under reduced pressure, and crystals separated out therefrom were collected by filtration to give ethyl-2-acetylmethylmercapto-4-hydroxy-6,7-methyl-enedioxyquinoline 3-carboxylate which was an intermediate compound. The resulting crystals were dissolved in five milliliters of concentrated sulfuric acid, the solution was stirred at room temperature for thirty minutes, then poured over into twenty milliliters of ice water, and crystals separated out therefrom were collected by filtration. The crystals were well washed with water and then washed with ethyl ether. Then the crystals were dried under reduced pressure to give 470 mg of the title compound melting at 308° to 311° C. Elementary analysis calculated as $C_{16}H_{13}NO_5S$: C 58.00, H 3.95, N 4.23; Found: C 58.21, H 3.90, N 4.11.

Infrared absorption spectra (KBr, cm$^{-1}$): 1645, 1610, 1590, 1310, 1040.

Nuclear magnetic resonance spectra $\delta$($CF_3CO_2D$): 1.70 (3H, triplet, —$OCH_2\underline{CH_3}$), 3.22 (3H, singlet, —$CH_3$), 4.84 (2H, quartet, —$O\underline{CH_2}CH_3$), 6.33 (2H, singlet, —$OCH_2O$—), 7.60 (1H, singlet, $C_9$—H), 7.97 (1H, singlet, $C_6$—H), 8.25 (1H, singlet, $C_2$—H).

EXAMPLE 67

1-Methyl-7,8-methylenedioxy-5-oxo-5H-thiazolo(3,2-a)quinoline-4-carboxylic acid Ethyl 1-methyl-7,8-methylenedioxy-5-oxo-5H-thiazolo(3,2-a)quinoline-4-carboxylate (470 mg) was dissolved in a solution of 550 mg of potassium carbonate in a mixture of 20 ml of water and 80 ml of ethanol and the whole mixture was heated to reflux for two hours with stirring. After the reaction was completed, ethanol was evaporated therefrom under reduced pressure, the residue was poured over into twenty milliliters of ice water, and neutralized with acetic acid. Crystals separated out therefrom were collected by filtration, washed with water, and then with ethanol and ether. Then it was recrystallized from fifty milliliters of dimethyl formamide to give 360 mg of the title compound melting at 303° to 305° C. Elementary analysis calculated as $C_{14}H_9NO_5S$: C 55.44, H 2.99, N 4.62; Found: C 55.42, H 2.66, N 4.51.

Infrared absorption spectra (KBr, cm$^{-1}$): 3400 to 3500, 1680, 1500, 1260, 1040.

Nuclear magnetic resonance spectra $\delta$($CF_3CO_2D$): 3.23 (3H, singlet, —$CH_3$), 6.35 (2H, singlet, —$OCH_2O$—), 7.60 (1H, singlet, $C_9$—H), 7.96 (1H, singlet, $C_6$—H), 8.23 (1H, singlet, $C_2OH$).

EXAMPLE 68

Ethyl 1-chloromethyl-7,8-methylenedioxy-5-oxo-5H-thiazolo(3,2-a)-quinoline-4-carboxylate One gram of ethyl 4-hydroxy-2-mercapto-6,7 methylenedioxyquinoline 3-carboxylate was dissolved in sodium ethoxide prepared from 86 mg of sodium and 50 ml of ethanol and the mixture was stirred for thirty minutes at room temperature. Then a mixture of 431 mg of dichloroacetone and 30 ml of ethanol was dropped therein and the whole mixture was stirred at room temperature for four hours. After the reaction was completed, crystals separated out therefrom were collected by filtration to give 1.1 grams of ethyl 2-(1-chloroacetylmethylmercapto)-4-hydroxy-6,7-methylenedioxyquinoline-3-carboxylate melting at 184° C. The resulting crystals were dissolved in ten milliliters of concentrated sulfuric acid with ice cooling and the mixture was stirred for one hour. After the reaction was completed, the reaction solution was poured over into fifty milliliters of ice water, the mixture was neutralized with an aqueous solution (2N) of sodium hydroxide, and crystals separated out therefrom were collected by filtration. The crystals were well washed with water and recrystallized from one hundred milliliters of dimethyl formamide to give 600 mg of the title compound which melted at higher than 320° C. Elementary analysis calculated as $C_{16}H_{12}NO_5SCl$: C 52.54, H 3.31, N. 3.83; Found C 52.81, H. 3.43, N 3.99.

Infrared absorption spectra (KBr, cm$^{-1}$): 1650, 1630, 1600, 1580, 1470, 1050.

Nuclear magnetic resonance spectra $\delta$($CF_3CO_2D$): 1.70(3H, triplet, —$OCH_2\underline{CH_3}$), 4.85 (2H, quartet, —$O\underline{CH_2}CH_3$), 5.3 (2H, singlet, —$\underline{CH_2}Cl$), 6.35 (2H, singlet, —$OCH_2O$—), 7.98 (1H, singlet, $C_9$—H), 8.02 (1H, singlet, $C_6$—H), 8.35 (1H, singlet, $C_2$—H).

EXAMPLE 69

1-methoxymethyl-7,8-methylenedioxy-5-oxo-5H-thiazolo(3,2-a)-quinoline-4-carboxylic acid Metal sodium (78 mg) was dissolved in thirty milliliters of methanol, 600 mg of ethyl 1-chloromethyl-7,8-methylenedioxy-5-oxo-5H-thiazolo(3,2-a)quinoline 4-carboxylate was added thereto at a time with stirring at room temperature and the whole mixture was heated to reflux with stirring for three hours. After the reaction was completed, methanol was evaporated therefrom under reduced pressure, crystals separated out thereby were collected by filtration, and washed well with water. The resulting crystals were dissolved in ethyl acetate, purified by passing through a column (150 g of silica gel), and ethyl acetate in the resulting solution was evaporated therefrom to give 300 mg of methyl 1-methoxymethyl-7,8-methylenedioxy-5-oxo-5H-thiazolo(3,2-a)quinoline 4-carboxylate.

The resulting crystals were dissolved in a solution of one hundred milligrams of sodium hydroxide in a mixture of 25 ml of water and 25 ml of ethanol and the mixture was heated to reflux for three hours with stirring. After the reaction was completed, it was cooled with ice, neutralized with acetic acid, crystals separated out therefrom were collected by filtration, and well washed with water. The resulting crystals were dried by heating under reduced pressure to give 250 mg of the title compound melting at 265° C.

Infrared absorption spectra (KBr, cm$^{-1}$): 3.79 (3H, singlet, —OCH$_3$), 5.18 (2H, singlet, —CH$_2$—OCH$_3$), 6.35 (2H, singlet, —OCH$_2$O—), 7.96 (1H, singlet, C$_9$—H), 8.06 (1H, singlet, C$_6$—H), 8.32 (1H, singlet, C$_2$—H).

EXAMPLE 70

Ethyl 6,7-methylenedioxy-4-oxo-4H-(1,3)thiazeto(3,2-a)-quinoline-3-carboxylate A mixture of 500 mg of ethyl 4-hydroxy-2-mercapto-6,7-methylene-dioxyquinoline-3-carboxylate and 510 mg of potassium carbonate was added to 300 ml of dimethyl formamide and the whole mixture was stirred at room temperature. Then 660 mg of diiodomethane was dropped thereinto and the mixture was stirred at room temperature for two hours. After the reaction was completed, dimethyl formamide was evaporated therefrom under reduced pressure and the residue was poured over into 50 ml of ice water. Crystals separated out thereby were collected by filtration and washed with water and with ethanol and finally dried with air to give 450 mg of the title compound. Elementary analysis calculated as C$_{14}$H$_{11}$NO$_5$S: C 55.08, H 3.63, N 4.59; Found: C 55.21, H 3.81, N 4.41.

Infrared absorption spectra (KBr,cm$^{-1}$): 1710, 1625, 1370, 1020.

Nuclear magnetic resonance spectra δ(CF$_3$CO$_2$D): 1.50 (3H, triplet, —OCH$_2$CH$_3$), 4.68 (2H, quartet, —OCH$_2$CH$_3$). 6.08 (2H, singlet, C$_2$—H), 6.30 (2H, singlet, —OCH$_2$—O), 7.02 (1H, singlet, C$_7$—H), 7.72 (1H, singlet, C$_4$—H).

EXAMPLE 71

Ethyl 8,9-methylenedioxy-6-oxo-1,2,3,6-tetrahydro(1,3)-thiazino(3,2-a)-quinoline-4-carboxylate A mixture of 500 mg of ethyl 4-hydroxy-2-mercapto-6,7-methylenedioxyquinoline-3-carboxylate and 510 mg of potassium carbonate was added to 30 ml of dimethyl formamide and the whole mixture was stirred at room temperature. Then 520 mg of 1,3-dibromopropane was dropped thereinto and the mixture was stirred at room temperature for thirty minutes. After the reaction was completed, dimethyl formamide was evaporated therefrom under reduced pressure and the residue was poured over into 20 ml of ice water. Crystals separated out therefrom were collected by filtration, washed with water, methanol and ether, and dried with air to give 330 mg of the title compound. Elementary analysis calculated as C$_{16}$H$_{15}$NO$_5$S: C 57.65, H 4.54, N 4.20; Found: C 57.45, H 4.61, N 4.11.

Infrared absorption spectra (KBr, cm$^{-1}$): 1720, 1620, 1580, 1480.

Nuclear magnetic resonance spectra δ(CF$_3$CO$_2$D): 1.56 (3H, triplet, —OCH$_2$CH$_3$), 2.30 to 3.00 (2H, multiplet, C$_2$—H), 3.30 (2H, triplet, C$_3$—H), 4.30 to 5.00 (4H, multiplet, —OCH$_2$CH$_3$ and C$_1$—H), 6.25 (2H, singlet, —OCH$_2$O—), 7.41 (1H, singlet, C$_{10}$—H), 7.73 (1H, singlet, C$_7$—H).

EXAMPLE 72

8,9-methylenedioxy-6-oxo-1,2,3,6-tetrahydro-(1,3)thiazino(3,2-a)-quinoline-4-carboxylic acid Ethyl 8,9-methylenedioxy-6-oxo-1,2,3,6-tetrahydro-(1,3)thiazino(3,2-a)-quinoline-4-carboxylate (510 mg) was dissolved in a solution of one gram of potassium hydroxide in a mixture of 25 ml of water and 25 ml of ethanol. The whole mixture was heated to reflux for two hours. After the reaction was completed, ethanol was evaporated therefrom under reduced pressure, the residue was poured over into thirty milliliters of ice water, neutralized with acetic acid, crystals separated out thereby were collected by filtration, washed with water, ethanol and ether, and recrystallized from 30 ml of dimethyl formamide to give 310 mg of the title compound which melted at 274° to 284° C. Elementary analysis calculated as C$_{14}$H$_{11}$NO$_5$S: C 55.01, H 3.63, N 4.59; Found: C 55.31, H 3.82, N 4.60.

Infrared absorption spectra (KBr, cm$^{-1}$): 3400 to 3500, 1685, 1500, 1260, 1060.

Nuclear magnetic resonance spectra δ(CF$_3$CO$_2$D); 2.50 to 3.0 (2H, multiplet, C$_2$—H), 3.35 (2H, triplet, J=6.0 Hz, C$_3$—H), 4.68 (2H, triplet, C$_1$-H), 6.29 (2H, singlet, —OCH$_2$O—), 7.42 (1H, singlet, C$_{10}$—H), 7.76 (1H, singlet, C$_7$—H).

EXAMPLE 73

7-fluoro-8-(4-formyl-1-piperazinyl)-5-oxo-5H-thiazolo(3,2-a)-quinoline-4-carboxylic acid 7-fluoro-5-oxo-8-(1-piperazinyl)-5H-thiazolo(3,2-a)-quinoline-4-carboxylic acid (350 mg) was dissolved in 15 ml of 98% concentrated formic acid, then 5 ml of acetic anhydride was dropped thereinto gradually with ice cooling, the reaction mixture was then stirred at room temperature for four hours, poured over into ice water, and crystals separated out therefrom were collected by filtration. The crystals were then washed with water and with ethanol and dried to give 310 mg of the title compound as colorless powder which melted at 335° to 336° C. with decomposition. Elementary analysis calculated as C$_{17}$H$_{14}$FN$_3$O$_4$.¼H$_2$O: C 53.75, H 3.85, N 11.06; Found: C 53.50, H 3.78, N 10.88.

Infrared absorption spectra (KBr, cm$^{-1}$): 3400, 1668, 1625, 1592, 1492, 1440, 1395, 1260, 1228, 1135, 1005, 802, 793.

Nuclear magnetic resonance spectra δ(CF$_3$CO$_2$D): 3.5 to 4.2 (8H, multiplet, methylene group in piperazine), 7.73 (1H, doublet, C$_9$—H), 7.94 (1H, doublet, C$_2$—H), 8.24 (1H, doublet, C$_6$—H), 8.35 (1H, singlet, —CHO), 8.87 (1H, doublet, C$_1$—H).

EXAMPLE 74

8-(4-acetyl-1-piperazinyl)-7-fluoro-5-oxo-5H-thiazolo(3,2-a)-quinoline-4-carboxylic acid 7-fluoro-5-oxo-8-(1-piperazinyl)-5H-thiazolo(3,2-a)-quinoline-4-carboxylic acid (400 mg) was dissolved in 60 ml of pyridine and the solution was heated to reflux at 70° C. for five hours with stirring after addition of 500 mg of acetic anhydride. After cooled, this was poured over into ice water, and crystals separated out therefrom were collected by filtration. The crystals were washed with water and ethanol to give 310 mg of the title compound as colorless powder which melted at 326° to 8° C. with decomposition. Elementary analysis calclulated as $C_{18}F_{17}FN_3O_4$: C 55.38, H 4.39, N 10.76; Found: C 55.13, H 4.05, N 10.49.

Infrared absorption spectra (KBr, cm$^{-1}$): 3400, 1680, 1655, 1630, 1590, 1247, 1223, 1118, 1041, 1000, 890, 802, 795, 730.

Nuclear magnetic resonance spectra $\delta(CF_3CO_2D)$: 2/68 (3H, singlet, =N—CO—$\underline{CH_3}$), 3.6 to 4.4 (8H, multiplet, methylene group in piperazine), 7.70 (1H, doublet, $C_9$—H), 7.95 (1H, doublet, $C_2$—H), 8.25 (1H, doublet, $C_6$—H), 8.88 (1H, doublet, $C_1$—H).

EXAMPLE 75

8-(4-(3-carboxypropionyl)-1-piperazinyl)-7-fluoro-5-oxo-5H-thiazolo(3,2-a)-quinoline-4-carboxylic acid A mixture of 350 mg of 7-fluoro-5-oxo-(1-piperazinyl)-5H-thiazolo(3,2-a)-quinoline-4-carboxylic acid, 150 mg of succinic anhydride, 30 ml of dimethyl formamide, and 5 ml of triethylamine was heated with stirring at 70° C. for three hours. After cooled, 300 ml of water was added to the reaction solution, the mixture was weakly acidified with acetic acid, and the resulting flowing gel-like substance was collected by filtration. This was washed with water and dried to give 350 mg of the title compound as pale brown powder which melted at 331° to 334° C. with decomposition. Elementary analysis calculated as $C_{20}H_{18}FN_3O_6S \cdot \frac{1}{2}H_2O$: C 53.69, H 4.20, N 9.21; Found: C 52.41, H. 4.01, N 9.00.

Infrared absorption spectra (KBr, cm$^{-1}$): 3420, 1690, 1628, 1490, 1392, 1260, 1227, 1140, 1012, 802, 795.

Nuclear magnetic resonance spectra $\delta(CF_3CO_2D)$: 3.05 (4H, singlet, —CO—$CH_2CH_2$—$CO_2H$), 3.50 to 4.35 (8H, multiplet, methylene group in piperazine), 7.73 (1H, doublet, $C_9$—H), 7.97 (1H, doublet, $C_2$—H), 8.27 (1H, doublet, $C_6$—H), 8.90 (1H, doublet, $C_1$—H).

EXAMPLE 76

8-(4-(4-carboxybutyroyl)-1-piperazinyl)-7-fluoro-5-oxo-5H-thiazolo(3,2-a)-quinoline-4-carboxylic acid A mixture of 210 mg of 7-fluoro-5-oxo-8-(1-piperazinyl)-5H-thiazolo(3,2-a)-quinoline-4-carboxylic acid, 82 mg of glutaric anhydride, 18 ml of dimethyl formamide and 3 ml of triethylamine was heated with stirring at 60° C. for two hours. After cooled, 60 ml of water was added thereto, then made weakly acidic with acetic acid, chloroform was added thereto, the mixture was stirred for ten minutes, and crystals separated out thereby were collected by filtration. The crystals were washed with water, ethanol and ether and dried to give 245 mg of the title compound as colorless powder which melted at 276° to 278° C. Elementary analysis calculated as $C_{21}H_{20}FN_3O_6S \cdot \frac{1}{2}H_2O$: C 53.61, H 4.49, N 8.93; Found C 53.89, H 4.42 N 8.85.

Infrared absorption spectra (KBr, cm$^{-1}$): 3430, 1700, 1627, 1590, 1480, 1390, 1260, 1220, 1140, 1030, 802, 795.

Nuclear magnetic resonance spectra $\delta(CF_3CO_2D)$: 1.90 (2H, multiplet, —CO$CH_2\underline{CH_2}CH_2CO_2H$), 2.50 to 3.20 (4H, multiplet, —CO$\underline{CH_2}CH_2\underline{CH_2}CO_2H$), 3.50 to 4.35 (8H, multiplet, methylene group in piperazine), 7.57 (1H, doublet, $C_9$—H), 8.00 (1H, doublet, $C_2$—H), 8.28 (1H, doublet, $C_6$—HO, 8.92 (1H, doublet, $C_1$—H).

EXAMPLE 77

7-fluoro-5-oxo-8-(4-palmitoyl-1-piperazinyl)-5H-thiazolo(3,2-a)-quinoline-4-carboxylic acid A mixture of 210 mg of 7-fluoro-5-oxo-8-(1-piperazinyl)-5H-thiazolo(3,2-a)-quinoline-4-carboxylic acid, 197 mg of palmitoyl chloride, 36 ml of dimethyl formamide and 6 ml of triethylamine was heated with stirring at 70° C. for three hours and then the solvent was evaporated therefrom under reduced pressure. Water was added to the residue and the mixture was extracted with cloroform. The chloroform extract was washed with water, dried with magnesium sulfate, and chloroform was evaporated therefrom to give a dark yellow, thick oily residue. This was subjected to separation and purification with silica gel chromatography to give 100 mg of the title compound as a colorless waxy substance. Elementary analysis calculated as $C_{32}H_{44}FN_3O_4$: C 65.61, H 7.57, N 7.17; Found: C 65.44, H 7.82, N 6.80.

Infrared absorption spectra (KBr, cm$^{-1}$): 1690, 1650, 1625, 1490, 1260, 1218, 1138, 1025, 897, 802, 792.

Nuclear magnetic resonance spectra $\delta(CDCl_3)$: 0.86 (3H, singlet, $\underline{CH_3}$—$(CH_2)_{14}CO$—), 1.24 (26H, singlet, $CH_2(\underline{CH_2})_{13}\underline{CH_2}CO$—), 2.35 (2H, triplet, $C_{14}H_{29}$—$\underline{CH_2CO}$—), 3.20 to 3.55 (4H, broad singlet, protons at 2- and 6-positions of piperazine), 3.55 to 4.00 (4H, broad singlet, protons at 3- and 5-positions of piperazine), 7.13 (1H, doublet, $C_9$—H), 7.27 (1H, doublet, $C_2$—H), 7.78 (1H, doublet, $C_6$—H), 8.14 (1H, doublet, $C_1$—H).

EXAMPLE 78

8-(4-(2-carboxybenzoyl)-1-piperazinyl)-7-fluoro-5-oxo-5H-thiazolo(3,2-a)-quinoline-4-carboxylic acid A mixture of 210 mg of 7-fluoro-5-oxo-8-(1-piperazinyl)-5H-thiazolo(3,2-a)quinoline 4-carboxylic acid, 108 mg of phthalic anhydride, 18 ml of dimethyl formamide, and 3 ml of triethylamine was stirred with heating at 60° C. for two hours. After cooled, water was added thereto and the mixture was weakly acidified with acetic acid. The resulting floating substances were collected by filtration, washed with water and dried to give 200 mg of the title compound as a pale yellow powder which melted at 277° to 278° C. Elementary analysis calculated as $C_{24}H_{22}FN_3O_6S \cdot 2H_2O$: C 54.24, H 4.17, N 7.91; Found: C 53.95, H 3.74, N 7.78.

Infrared absorption spectra (KBr, cm$^{-1}$): 3480, 1700, 1628, 1490, 1445, 1400, 1263, 1428, 1142, 1009, 800.

Nuclear magnetic resonance spectra $\delta(CF_3CO_2D)$: 3.55 to 4.20 (8H, multiplet, methylene group in piperazine), 7.87 (1H, doublet, $C_9$—H), 8.02 (5H, multiplet, proton in benzene ring and $C_2$—H), 8.30 (1H, doublet, $C_6$—H), 8.97 (1H, doublet, $C_1$—H).

The compounds of the invention are used to treat bacterial and fungal infections in mammals by administering to the sufferer an anti-bacterial or anti-fungal amount of the compound of the invention, preferably in the form of a pharmaceutical composition comprising an anti-bacterial or anti-fungal amount of the compound in combination with a pharmaceutically acceptable, non-toxic, inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses, or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present. Generally, the pharmaceutical composition will contain from about 0.01 to about 70%, preferably about 0.1 to about 5% by weight of the compound of the invention.

Although the dosage and dosage regimen must in each case be carefully adjusted, utilizing sound professional judgment and considering the age, weight and condition of the recipient, the route of administration and the nature and gravity of the illness, generally the dosage be from 0.1 to 150 mg of the compound of the present invention, preferably 5 to 20 mg, per kg of body weight per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders were prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free-flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of non-toxic alcoholic vehicles. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccarin, and the like, can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or deaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories, in which the compound is admixed with low-melting, water-soluble or insoluble solids such as polyethylene glycol, cocoa butter, higher esters as for example myristyl palmitate, or mixtures thereof.

While the routes of administration of the compound of the invention include oral, parenteral (i.e. intramuscular, intraperitoneal and intravenous), and rectal, oral and parenteral administration is particularly preferred.

The preferred pharmaceutical compositions are therefore those in a form suitable for oral and parenteral administration, such as tablets, liquids, and parenteral solutions.

When used for as antifungal agents, the compounds of the invention are preferably administered topically, as by painting, coating, dusting or spraying, and preferably in the form of a topical pharmaceutical composition, such as a liquid, cream, emulsion, powder, paste, ointment, spray or the like.

What is claimed is:

1. A compound of the formula

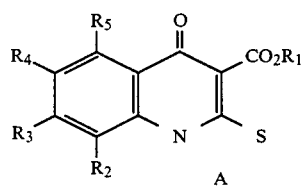

$R_1$ is hydrogen, alkali metal, alkaline earth metal, lower alkyl, pivaloyloxymethyl or phthalidyl;

$R_2$, $R_3$, $R_4$ and $R_5$ are the same or different and are hydrogen, halogen, lower alkoxy or

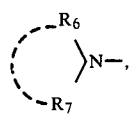

wherein R₆ and R₇ are lower alkyl or R₆ and R₇ together with the nitrogen atom to which they are attached form a five- to seven-membered heterocyclic ring having said nitrogen atom as the sole hetero atom or having nitrogen, sulfur or oxygen as additional hetero atoms, said heterocyclic ring being unsubstituted or substituted by lower alkyl, lower alkenyl, hydroxy(lower alkyl), (lower alkoxy) (hydroxy)lower alkyl, phthalidyl, formyl, acetyl, carboxypropionyl, carboxybutyroyl, palmitoyl or carboxybenzoyl;

A is an unsaturated hydrocarbon chain of one to five carbon atoms, unsubstituted or substituted by lower alkyl; lower alkoxy; lower alkylthio; hydroxy; halogen; lower alkyl substituted by halogen, amino, loweralkoxycarbonyl, carboxy, loweralkoxy, loweralkylthio, loweracyloxy or hydroxy; loweralkylamino; carboxy; nitro; cyano; carbonyl; imino; or by substituted or unsubstituted phenyl, phenylthio, phenylamino or phenoxy; or A is

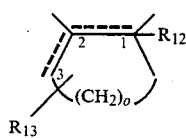

wherein o is 1 or 2 and the dotted line is a double bond between the depicted 1- and 2- or 2- and 3-positions, R₁₂ is not present when said double bond is between 1- and 2-positions or is hydrogen, lower alkyl or phenyl when said double bond is between 2- and 3-positions, and R₁₃ is hydrogen, lower alkyl or phenyl; and R₂ and R₃ or R₃ and R₄ or R₄ and R₅ together may be alkylenedioxy of 1 to 5 carbon atoms which form a ring with the carbon atoms to which they are attached; or a pharmaceutically acceptable salt thereof.

2. The compound according to claim 1, wherein A is said unsubstituted or substituted unsaturated hydrocarbon chain of one to five carbon atoms.

3. The compound according to claim 2, wherein A has one unsaturated carbon-to-carbon double bond.

4. The compound according to claim 1, wherein one or two of R₂, R₃, R₄ and R₅ is said

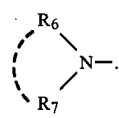

5. The compound according to claim 1, wherein aid heterocyclic ring has one of said additional hetero atoms.

6. The compound according to claim 1, wherein R₂ is hydrogen, halogen or lower alkoxy;

R₃ is hydrogen, halogen, lower alkoxy or piperazinyl unsubstituted or substituted by lower alkyl, lower alkenyl, (hydroxy) lower alkyl, (lower alkoxy) (hydroxy) lower alkyl, or phthalidyl;

R₄ is hydrogen, halogen or lower alkoxy; or

R₃ and R₄ together with the carbon atoms to which they are attached, form a 5, 6 or 7-membered ring containing carbon atoms and 1 or 2 oxygen atoms; and R₅ is hydrogen, halogen, lower alkoxy or piperazinyl unsubstituted or substituted by lower alkyl, lower alkenyl, hydroxy(lower alkyl) or (lower alkoxy) (hydroxy) lower alkyl, or phthalidyl; provided that at least one of said R₃ and R₅ is said unsubstituted or substituted piperazinyl.

7. 7-fluoro-1-methyl-8-(4-methyl-1-piperazinyl)-5-oxo-5H-thiazolo(3,2-a)quinoline-4-carboxylic acid.

8. The compound according to claim 1, which is 7-fluoro-5-oxo-8-(1-piperazinyl)-5H-thiazolo-(3,2,a)-quinoline-4-carboxylic acid, 7-fluoro-8-(4-methyl-1-piperazinyl)-5-oxo-5H-thiazolo(3,2a)quinoline-4-carboxylic acid, 8-(4 allyl-1-piperazinyl)-7-fluoro-5-oxo-5H-thiazolo(3,2,a)-quinoline-4-carboxylic acid, or 7-fluoro-1-methyl-5-oxo-8-(1-piperazinyl)-5H-thiazolo(3,-2,a)quinoline-4-carboxylic acid.

9. The compound according to claim 3, wherein said chain contains two carbon atoms.

10. The compound according to claim 1, wherein A is

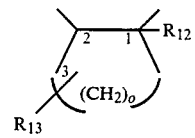

wherein o is 1 or 2 and the dotted line is a double bond between the depicted 1- and 2- or 2- and 3-positions, R₁₂ is not present when said double bond is between said 1- and 2-positions or is hydrogen, lower alkyl or phenyl when said double bond is between said 2- and 3-positions, and R₁₃ is hydrogen, lower alkyl or phenyl.

11. The compound according to claim 10, wherein R₁₂ and R₁₃ are hydrogen or lower alkyl.

12. 8-Chloro-1-methyl-7-(4-methyl-4-piperazinyl)-5-oxo-5H-thiazolo(3,2,a)-quinoline-4-carboxylic acid.

13. A pharmaceutical composition for treatment of bacterial and fungal infections which comprises an antibacterial or anti-fungal effective amount of the compound according to claim 1 in combination with a pharmaceutically acceptable carrier or diluent therefor.

14. A method of treatment of bacterial or fungal infections in mammals, which comprises administering to the sufferer an anti-bacterial or anti-fungal effective amount of the compound according to claim 1.

* * * * *

UNITED STATES PATENT AND TRADEMARK OFFICE
CERTIFICATE OF CORRECTION

PATENT NO. : 4,659,734
DATED : April 21, 1987
INVENTOR(S) : Hiroshi Enomoto et al It is certified that error appears in the above-identified patent and that said Letters Patent are hereby corrected as shown below: On The Title Page:

In the Abstract, col. 1, lines 10-15 and
col. 56, lines 50-55, formula (I)
should read as follows:

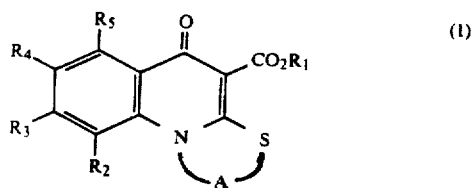

Signed and Sealed this

First Day of November, 1988

Attest:

DONALD J. QUIGG

Attesting Officer    Commissioner of Patents and Trademarks